United States Patent
Ladner et al.

(10) Patent No.: US 10,457,673 B2
(45) Date of Patent: *Oct. 29, 2019

(54) HETEROATOM CONTAINING DEOXYURIDINE TRIPHOSPHATASE INHIBITORS

(71) Applicant: University of Southern California, Los Angeles, CA (US)

(72) Inventors: Robert D. Ladner, Belfast (GB); Bruno Giethlen, Altorf (FR)

(73) Assignee: University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/719,165

(22) Filed: Sep. 28, 2017

(65) Prior Publication Data

US 2018/0086746 A1 Mar. 29, 2018

Related U.S. Application Data

(63) Continuation of application No. 15/109,616, filed as application No. PCT/US2015/010059 on Jan. 2, 2015, now Pat. No. 9,790,214.

(60) Provisional application No. 61/923,534, filed on Jan. 3, 2014.

(51) Int. Cl.

| | |
|---|---|
| *C07D 413/06* | (2006.01) |
| *C07D 403/06* | (2006.01) |
| *A61K 31/496* | (2006.01) |
| *A61K 31/513* | (2006.01) |
| *A61K 31/5377* | (2006.01) |
| *C12Q 1/6876* | (2018.01) |

(52) U.S. Cl.
CPC .......... *C07D 413/06* (2013.01); *A61K 31/496* (2013.01); *A61K 31/513* (2013.01); *A61K 31/5377* (2013.01); *C07D 403/06* (2013.01); *C12Q 1/6876* (2013.01); *C12Q 2600/158* (2013.01)

(58) Field of Classification Search
CPC ................ A61K 31/496; A61K 31/513; A61K 31/5377; C07D 403/06; C07D 413/06; C12Q 1/6876; C12Q 2600/158
See application file for complete search history.

(56) References Cited

U.S. PATENT DOCUMENTS

| | | | |
|---|---|---|---|
| 4,304,715 A | 12/1981 | Hudson et al. | |
| 4,868,303 A | 9/1989 | Takase et al. | |
| 5,077,288 A * | 12/1991 | Lavielle | C07D 211/32 514/210.01 |
| 5,599,796 A | 2/1997 | Schinazi et al. | |
| 5,962,246 A | 10/1999 | Ladner et al. | |
| 6,268,365 B1 | 7/2001 | Betageri et al. | |
| 7,601,702 B2 | 10/2009 | Gilbert et al. | |
| 8,530,490 B2 | 9/2013 | Fukuoka et al. | |
| 9,809,571 B2 | 11/2017 | Ladner et al. | |
| 2010/0075924 A1 | 3/2010 | Gilbert et al. | |
| 2011/0021459 A1 | 1/2011 | Gilbert et al. | |
| 2011/0082163 A1 | 4/2011 | Fukuoka et al. | |
| 2011/0212467 A1 | 9/2011 | Ladner et al. | |
| 2011/0306551 A1 | 12/2011 | Zundel et al. | |
| 2012/0225838 A1 | 9/2012 | Fukuoka et al. | |
| 2016/0039788 A1 | 2/2016 | Ladner et al. | |
| 2016/0326149 A1 | 11/2016 | Ladner et al. | |

FOREIGN PATENT DOCUMENTS

| | | |
|---|---|---|
| CN | 102056905 A | 5/2011 |
| EP | 1 939 186 | 7/2008 |
| EP | 2 295 414 | 3/2011 |
| EP | 2 508 185 | 10/2012 |
| JP | 48-029785 | 4/1973 |
| JP | S5839672 | 3/1983 |
| JP | 63-101361 | 5/1988 |
| JP | 09-500872 | 1/1997 |
| JP | H09-286786 | 11/1997 |
| JP | 2002-284686 | 10/2002 |
| JP | 2003-524641 A | 8/2003 |
| JP | 2005-526029 A | 9/2005 |
| WO | WO-00/59874 | 10/2000 |
| WO | WO-02/083651 | 10/2002 |
| WO | WO-2005/065689 | 7/2005 |
| WO | WO-2005/066160 | 7/2005 |
| WO | WO-2006/081251 | 8/2006 |
| WO | WO-2008/016522 | 2/2008 |
| WO | WO-2009/074575 | 6/2009 |
| WO | WO-2009/147843 | 12/2009 |

(Continued)

OTHER PUBLICATIONS

Wolfe, et al., Dianions derived from glutarimide, 3,5-morpholinedione, and 3,5-thiomorpholinedione as useful new synthetic intermediates, J. of Org. Chem., 35(11), 3600-7 (1970). (Year: 1970).*
Extended European Search Report dated Dec. 19, 2017, from application No. 15733304.8.
Non-Final Office Action dated Jun. 27, 2018, from U.S. Appl. No. 15/711,680.
"DUTPase inhibition augments replication defects of 5-Fluorouracil," www.impactjournals.com/oncotarget/, Oncotarget, Supplementary Materials 2017.
"Pubchem SID 165224215" Create Date: Nov. 15, 2013 (Nov. 15, 2013) Date Accessed: Nov. 7, 2016 (Nov. 7, 2016).
Adlard J W et al. (2004), "Assessment of multiple markers for association with response rate (RR) and failure-free survival (FFS) in patients with advanced colorectal cancer (CRC) treated with chemotherapy in the MRC CR08 (FOCUS) randomized trial", Journal of Clinical Oncology, 2004 ASCO Annual Meeting Proceedings (Post-Meeting Edition), vol. 22, No. 14S (Jul. 15 Supplement), 2004: 9506.

(Continued)

*Primary Examiner* — Erich A Leeser
(74) *Attorney, Agent, or Firm* — Foley & Lardner LLP; Antoinette F. Konski; Alice Lee-Dutra

(57) ABSTRACT

Provided herein are dUTPase inhibitors, compositions comprising such compounds and methods of using such compounds and compositions in a method of treating cancer. The dUTPase inhibitors disclosed contain a uracil isostere in the molecule represented by a 2,6-diketopiperazine moiety. Thioanalogs of the uracil isostere where a thione replaces each of the ketone are also disclosed.

7 Claims, No Drawings

(56) References Cited

FOREIGN PATENT DOCUMENTS

| | | |
|---|---|---|
| WO | WO-2010/023946 | 3/2010 |
| WO | WO-2011/065541 | 6/2011 |
| WO | WO-2011/065545 | 6/2011 |
| WO | WO-2011/078370 | 6/2011 |
| WO | WO-2012/069658 A2 | 5/2012 |
| WO | WO-2014/107622 | 7/2014 |
| WO | WO-2015/103489 A1 | 7/2015 |
| WO | WO-2016/175324 | 11/2016 |
| WO | WO-2016/178416 | 11/2016 |
| WO | WO-2006/135763 | 12/2016 |
| WO | WO-2017/006270 A1 | 1/2017 |
| WO | WO-2017/006271 A1 | 1/2017 |
| WO | WO-2017/006282 A1 | 1/2017 |
| WO | WO-2017/006283 A1 | 1/2017 |

OTHER PUBLICATIONS

Beaven A W et al. (2006), "Adjuvant therapy for colorectal cancer: yesterday, today, and tomorrow", Oncology, 20(5).

Briganti, et al., "Sulfonylamido derivatives of aminoglutethimide and their copper(II) complexes: a novel class of antifungal compounds", Eur J Med Chem (1997) 32, 901-910.

Database CAPLUS in STN, Acc. No. 2002-675781, Reddy et al., WO2002067865 A2 (Sep. 6, 2002) (abstract).

European Partial Search Report dated May 17, 2017, from application No. 15733304.8.

File Registry on STN, RN:1266691-63-7, Entered STN: Mar. 8, 2011.

File Registry on STN, RN:1266695-69-5, Entered STN: Mar. 8, 2011.

File Registry on STN, RN:889965-68-8, Entered STN: Jun. 29, 2006.

Hagenkort, et al., "dUTPase inhibition augments replication defects of 5-Fluorouracil," published Feb. 28, 2017, www.impactjournals.com/oncotarget/, Oncotarget, Advance Publications 2017.

Hayes C J et al. (2009), "Bridgehead Lithiation-Substitution of Bridged Ketones, Lactones, Lactams, and Imides: Experimental Observations and Computational Insights", J. Am. Chem. Soc., 132(23).

Huang Z et al. (2001), "A novel kind of antitumor drugs using sulfonamide as parent compound", Eur. J. Med. Chem. 2001, 36.

Koehler S E et al. (2004), "Small interfering RNA-mediated suppression of dUTPase sensitizes cancer cell lines to thymidylate synthase inhibition", Mol Pharmacol. Sep. 2004;66(3).

Ladner R D (2001), "The role of dUTPase and uracil-DNA repair in cancer chemotherapy", Curr Protein Pept Sci, 2001. 2(4).

Ladner R D et al. (1996), "Identification of a consensus cyclin-dependent kinase phosphorylation site unique to the nuclear form of human deoxyuridine triphosphate nucleotidohydrolase", J Biol Chem., 271(13).

Lora-Tamayo, M. et al., "Anticancerosos Potenciales I. Analogos Sulfonicos De Glutamina," Anales De La Real Sociedad Espanola De Fisica Y Quimica, Serie B: Quimica, Anales De La Real Sociedad Espanola De Fisica Y Quimica, Serie B: Quimica (1959), 55B, 527-32 Coden: Arsqal; ISSN: 0034-088X Madrid, ES, vol. 62, No. 2, Jan. 1, 1966 (Jan. 1, 1966).

Malamas M S (1994), "Facile synthesis of novel spiro[azetidine-2,4032(1032H)-isoquinoline-1032,3032,4(2032H)-triones]", Journal of Heterocyclic Chemistry, vol. 31, Issue 2.

Malamas M S et al. (1994), "N-Substituted Spirosuccinimide, Spiropyridazine, Spiroazetidine, and Acetic Acid Aldose Reductase Inhibitors Derived from Isoquinoline-1,3-diones. 2", J. Med. Chem., 37 (13).

Miyahara, et al., "Discovery of a Novel Class of Potent Human Deoxyuridine Triphosphatase Inhibitors Remarkably Enhancing the Antitumor Activity of Thymidylate Synthase Inhibitors", Journal of Medicinal Chem., 2012, 55.

Miyahara, et al., "Discovery of Highly Potent Human Deoxyuridine Triphosphatase Inhibitors Based on the Conformation Restirction Strategy". Journal of Medicinal Chem., 2012, 55.

Miyakoshi et al: "1,2,3-Triazole-Containing Uracil Derivatives with Excellent Pharmacokinetics as a Novel Class of Potent Human Deoxyuridine Triphophatase Inhibitors," Journal of Medicinal Chemistry, vol. 55, No. 14, Jul. 26, 2012 (Jul. 26, 2012) XP055109796, ISSN: 0022-2623, DOI: 10.1021/jm3004174.

Miyakoshi H et al. (2012), "Synthesis and discovery of N-carbonylpyrrolidine- or N-sulfonylpyrrolidine-containing uracil derivatives as potent human deoxyuridine triphosphatase inhibitors", 55(7).

Miyakoshi, et al., "1,2,3-Triazole-Containing Uracil Derivatives with Excellent Pharmacokinetics as a Novel Class of Potent Human Deoxyuridine Triphosphatase Inhibitors". Journal of Medicinal Chem., 2012, 55.

Mol C D et al. (1996), "Human dUTP pyrophosphatase: uracil recognition by a beta hairpin and active sites formed by three separate subunits", Structure. Sep. 15, 1996;4(9).

Ncbi: "SID 130780843," Pubchem Substance, Dec. 6, 2011 (Dec. 6, 2011), XP055302704, Retrieved from the Internet: URL: https://pubchem.ncbi.nlm.nih.gov/substance/130780843 [retrieved on Sep. 15, 2016].

Ncbi: "SID 38052934" In: "SID 38052934," Dec. 5, 2007 (Dec. 5, 2007), Pubchem Substance, XP055302701, DOI: https://pubchem.ncbi.clm.nih.gov/substance/38052934.

Nguyen C et al. (2005), "Deoxyuridine Triphosphate Nucleotidohydrolase as a Potential Antiparasitic Drug Target", J. Med. Chem. 2005, 48(19).

Nguyen C et al. (2006), "Acyclic Nucleoside Analogues as Inhibitors of Plasmodium falciparum dUTPase", J. Med. Chem. 2006, 49 (14).

Papamichael D (1999), "The Use of Thymidylate Synthase Inhibitors in the Treatment of Advanced Colorectal Cancer: Current Status", The Oncologist 1999, 4.

Patricia Peterli-Roth et al: "Syntheses of 6-Deaminosinefungin and (s)-6-Methyl-6-deaminosinefungin," The Journal of Organic Chemistry, vol. 59, No. 15, Jul. 1, 1994 (Jul. 1, 1994), pp. 4186-4193, XP055320022, US, ISSN: 0022-3263, DOI: 10.1021/jo00094a033.

Saito K et al. (2014), "First-in-human, phase I dose-escalation study of single and multiple doses of a first-in-class enhancer of fluoropyrimidines, a dUTPase inhibitor (TAS-114) in healthy male volunteers", Cancer Chemother Pharmacol (2014) 73.

Seiji Miyahara et al: "Discovery of a Novel Class of Potent Human Deoxyuridine Triphosphatase Inhibitors Remarkably Enhancing the Antitumor Activity of Thymidylate Synthase Inhibitors," Journal of Medicinal Chemstiry, vol. 55, No. 7, Apr. 12, 2012 (Apr. 12, 2012), XP055109868, ISSN: 0022-2623, DOI: 10.1021/jm201628y.

Seiji Miyahara et al: "Discovery of Highly Potent Human Deoxyuridine Triphosphatase Inhibitors Based on the Conformation Restriction Strategy," Journal of Medicinal Chemsitry, vol. 55, No. 11, Jun. 14, 2012 (Jun. 14, 2012), XP055109852, ISSN 0022-2623, DOI: 10.1021/jm300416h.

Takechi H et al. (2005), "Intramolecular photoreactions of thiohomophthalimides with an alkenyl group in their N-Side chain. Regioselective synthesis of heterocycle-fused isoquinoline derivatives through [2+2] photocycloaddition", Journal of Heterocyclic Chemistry, vol. 42, Issue 2.

Tinkelenberg B A et al. (2002), "dUTPase and uracil-DNA glycosylase are central modulators of antifolate toxicity in *Saccharomyces cerevisiae*", Cancer Res, 2002. 62(17).

U.S. Office Action dated Mar. 1, 2017, from U.S. Appl. No. 15/109,616.

U.S. Notice of Allowance dated Jul. 20, 2017, from U.S. Appl. No. 14/759,386.

U.S. Notice of Allowance dated Jun. 13, 2017, from U.S. Appl. No. 15/109,616.

Wilson P M et al. (2008), "Novel opportunities for thymidylate metabolism as a therapeutic target", Mol Cancer Ther, 2008. 7(9).

Wilson P M et al. (2012), "Inhibition of dUTPase Induces Synthetic Lethality with Thymidylate Synthase013Targeted Therapies in Non013Small Cell Lung Cancer", Mol. Cancer Ther. 11(3).

Zhou, J. et al. "Solid-Phase Synthesis of Potential Aspartic Acid Protease Inhibitors Containing a Hydroxyethylamine Istostere,"

(56) References Cited

OTHER PUBLICATIONS

Tetrahedron Letters, Pergamon, GB, vol. 40, No. 14, Apr. 2, 1999 (Apr. 2, 1999), pp. 2729-2732, XP004160293, ISSN: 0040-4039, DOI: 10.1016/S0040-4039(99)00351-2.
Database Registry Chemical Abstracts Service, Columbus, Ohio, Accession No. RN 100720-20-5, Entered STN: Mar. 8, 1986.
Database Registry Chemical Abstracts Service, Columbus, Ohio, Accession No. RN 92043-77-1, Entered STN: Nov. 16, 1984.
Mosher, et al., "Potential Anticancer Agents. VI. Synthesis of a-Amino-?-sulfamoylbutyric Acids with Substituents on the Sulfonamide Nitrogen", J. Org. Chem. 23(9), 1958, 1257-1261.
Non-Final Office Action dated Sep. 14, 2018, from U.S. Appl. No. 15/741,202.
Non-Final Office Action dated Sep. 14, 2018, from U.S. Appl. No. 15/914,958.
Notice of Allowance dated Oct. 16, 2018, from U.S. Appl. No. 15/711,680.
U.S. Office Action dated Oct. 19, 2018, from U.S. Appl. No. 15/740,783.
Banker, et al., "Modern Pharmaceutics", 1997, pp. 451 and 596.
McMahon, Gerald, "VEGF Receptor Signaling in Tumor Angiogenesis", The Oncologist, 2000; 5; pp. 3-10.
Pinedo, et al., "Translational Research: The Role of VEGF in Tumor Angiogenesis", The Oncologist, 2000; 5, pp. 1-2.
Vippagunta, et al., "Crystalline solids", Advanced Drug Delivery Reviews, 48 (2001), pp. 3-26.
International Search Report and Written Opinion dated Dec. 8, 2016, from application No. PCT/162016/054067.
International Search Report and Written Opinion dated Dec. 8, 2016, from application No. PCT/162016/054069.
International Search Report and Written Opinion issued in PCT/US2014/010247, dated Apr. 2, 2014.
International Search Report and Written Opinion issued in PCT/US2015/010059, dated Mar. 31, 2015.
Ito, et al., "A medium-term rat liver bioassay for rapid in vivo detection of carcinogenic potential of chemicals", Cancer Science, Jan. 2003, vol. 94, No. 1, pp. 3-8.
Non-Final Office Action dated Apr. 4, 2019, from U.S. Appl. No. 15/740,783.
STN Registry database entry for CAS RN 1390765-80-6, entry date of Aug. 14, 2012, Accessed Mar. 31, 2019.
STN Registry database entry for CAS RN 1638339-55-5, entry date of Dec. 10, 2014, Accessed Mar. 31, 2019.
STN Registry database entry for CAS RN 1825703-93-2, entry date of Dec. 9, 2015, Accessed Mar. 31, 2019.

* cited by examiner

HETEROATOM CONTAINING DEOXYURIDINE TRIPHOSPHATASE INHIBITORS

CROSS REFERENCE TO RELATED APPLICATIONS

This application is a continuation of U.S. application Ser. No. 15/109,616, filed Jul. 1, 2016, now U.S. Pat. No. 9,790,214, which is a National Stage Entry of International Patent Application No. PCT/US2015/010059, filed Jan. 2, 2015, which claims the benefit under 35 U.S.C. § 119(e) of U.S. Provisional Application Ser. No. 61/923,534, filed Jan. 3, 2014, the contents of each of which are incorporated herein by reference in their entirety.

BACKGROUND

Thymidylate metabolism is required for producing essential building blocks necessary to replicate DNA in dividing cells and has long been an important therapeutic target for cornerstone cancer drugs. Drugs targeting this pathway such as 5-fluorouracil (5-FU) inhibit the enzyme thymidylate synthase (TS) and are currently critical standard-of care therapies. TS-targeted agents are used for the treatment of a variety of cancers including colon, gastric, head and neck, breast, lung and blood related malignancies among others. Grem, J. L., 5-*Fluorouracil plus leucovorin in cancer therapy*, in *Principals and Practice of Oncology Update Series*, J. De Vita, V. T., S. Hellman, and A. Rosenberg, Editors. 1988, J. B. Lippincott: Philadelphia, Pa.

There are two classes of drugs that target the TS enzyme: the fluoropyrimidines and the antifolates. The fluoropyrimidines, 5-FU, S-1 and capecitabine (Xeloda®), have wide use in the treatment of gastrointestinal and breast cancers, while the antifolate pemetrexed (Alimta®) is currently used for the treatment of non-small cell lung cancer (NSCLC). Since the discovery of 5-FU over fifty years ago by Charles Heidelberger, the fluoropyrimidines remain one of the most common and effective anticancer cancer drugs used worldwide. Due to this fact, there is an abundance of clinical experience and insight into the mechanism of action of these agents.

The TS inhibitor 5-fluorouracil (5 FU) remains the foundation of many first and second line regimens in the treatment of colon cancer. Single agent therapies including oxaliplatin, irinotecan, Erbitux and Avastin, demonstrate lowered activity in colon cancer compared to 5-FU. In addition to colon cancer, TS-inhibitory agents have demonstrated efficacy in several other solid tumor types. Standard of care now incorporates 5-FU as the backbone drug in combination with oxaliplatin or irinotecan or another agent.

Deoxyuridine triphosphatase ("dUTPase") is a ubiquitous enzyme that is essential for viability in both prokaryotic and eukaryotic organisms; as the main regulator of dUTP pools, the expression of dUTPase could have profound effects on the utility of chemotherapeutics that inhibit thymidylate biosynthesis. Normally, dUTPase mediates a protective role by limiting the expansion of dUTP pools and countering the cytotoxic effect of uracil misincorporation. According to this model, elevated levels of dUTPase could prevent TS inhibitor-induced dUTP accumulation and induce drug resistance. It has been shown that dUTPase over expression results in a significant decrease in dUTP accumulation and increased resistance to drug treatment when compared to controls.

Chemotherapeutic agents that target de novo thymidylate metabolism are critical for the treatment of a variety of solid tumors, however clinical efficacy is often hindered by drug resistance. Because resistance to these agents is a common occurrence, the identification and exploitation of novel determinants of drug sensitivity within this pathway of proven therapeutic utility is important. As disclosed by Ladner et al. in U.S. Patent Publ. No. US 2011/0212467, the dUTPase enzyme and the uracil-DNA misincorporation pathway can play a driving role in mediating cytotoxicity to TS-directed chemotherapies.

For example, nearly half of cancer patients do not benefit from 5-FU-based treatment due to intrinsic or acquired drug resistance. Due to this fact, there is a critical need to overcome the fundamental challenge of drug resistance and provide new therapeutic strategies to improve patient outcome. This disclosure satisfies this need and provides related advantages as well.

SUMMARY

In some aspects, this disclosure provides compounds, compositions and methods that inhibit dUTPase when used alone or in combination with at least one dUTPase-directed chemotherapy. In some aspects, this disclosure provides compounds, compositions and methods for treating cancer, killing cancer cells, and inhibiting cancer cell growth when used in combination with at least one TS-directed chemotherapy. Compounds of this class include the following compounds of formulas (I), (II), and (III).

Thus, in one aspect, provided herein are compounds of formulas (I) and (II):

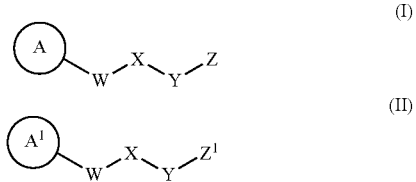

or a tautomer thereof, or a pharmaceutically acceptable salt and/or a solvate thereof, or a stereochemically pure or enriched stereoisomer of each thereof, wherein

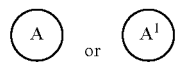

is a uracil isostere which is a 6 membered heterocycle comprising a —C(=V)—NH—C(=V)— moiety wherein V is independently O or S, and at least another ring heteroatom, and wherein the heterocyclic ring is optionally substituted, as provided hereinbelow;

W is a bond or optionally substituted —$CH_2$—;

X is a bond, O, S, $NR^{19}$, optionally substituted $C_1$-$C_6$ alkylene, optionally substituted $C_2$-$C_6$ alkenylene, or optionally substituted $C_2$-$C_6$ alkynylene group, a divalent optionally substituted $C_6$-$C_{10}$ aromatic hydrocarbon group, or a divalent optionally substituted saturated or unsaturated $C_2$-$C_{10}$ heterocyclic or optionally substituted $C_1$-$C_{10}$ heteroaryl group;

$R^{19}$ is hydrogen, optionally substituted $C_1$-$C_6$ alkyl or optionally substituted $C_3$-$C_8$ cycloalkyl;

Y is a bond or an optionally substituted $C_1$-$C_{10}$ alkylene which further optionally has a cycloalkylidene structure on one carbon atom, or is optionally substituted $C_2$-$C_6$ alkenylene, or optionally substituted $C_2$-$C_6$ alkynylene group, or Y is -$L^{10}$-$B^1$-$L^{11}$-;

$L^{10}$ and $L^{11}$ independently are optionally substituted $C_1$-$C_6$ alkylene, optionally substituted $C_2$-$C_6$ alkenylene, or optionally substituted $C_2$-$C_6$ alkynylene group;

$B^1$ is a divalent optionally substituted $C_6$-$C_{10}$ aromatic hydrocarbon group, or a divalent optionally substituted saturated or unsaturated $C_2$-$C_{10}$ heterocyclic or optionally substituted $C_1$-$C_{10}$ heteroaryl group;

Z is —$PO_2$—$NR^{31}R^{32}$, —$SO_2NR^{31}R^{32}$, —$NR^3PO_2$—$R^4$, —$NR^3SO_2$—$R^4$, or $R^4$ wherein $R^{31}$ and $R^{32}$ are the same or different and each represents a hydrogen atom, optionally substituted $C_1$-$C_6$ alkyl group optionally substituted with an aryl group, wherein the aryl group, together with the $R^{31}$ or $R^{32}$, may form a condensed bicyclic hydrocarbon, or $R^{31}$ and $R^{32}$ are taken together with the adjacent nitrogen atom form an optionally substituted $C_2$-$C_{10}$ heterocyclic group or an optionally substituted $C_1$-$C_{10}$ heteroaryl group;

$Z^1$ is —$PO_2$—$NR^{31}R^{32}$ or —$(OR^3)P(O)$—$R^4$ wherein $R^{31}$ and $R^{32}$ are independently a hydrogen atom, optionally substituted $C_1$-$C_6$ alkyl group optionally substituted with an aryl group, wherein the aryl group, together with the $R^{31}$ or $R^{32}$, may form a condensed bicyclic hydrocarbon, or $R^{31}$ and $R^{32}$ taken together with the adjacent nitrogen atom form an optionally substituted $C_2$-$C_{10}$ heterocyclic group or an optionally substituted $C_1$-$C_{10}$ heteroaryl group;

$R^3$ is hydrogen or optionally substituted $C_1$-$C_6$ alkyl; and $R^4$ is optionally substituted $C_6$-$C_{10}$ aryl, an optionally substituted $C_2$-$C_{10}$ heterocyclic group, or an optionally substituted $C_1$-$C_{10}$ heteroaryl group.

In another aspect, provided herein are compounds of formula (III):

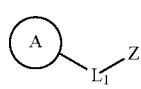

(III)

wherein A is

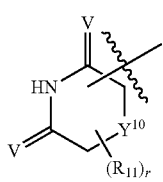

each V is independently O or S, $R^{11}$ is hydrogen, halo, $R^{12}$ or —O—$R^{12}$, wherein $R^{12}$ is $C_1$-$C_6$ alkyl, $C_2$-$C_6$ alkenyl, or $C_2$-$C_6$ alkynyl optionally substituted with 1-3 hydroxy, fluoro, chloro, and amino substituent, r is 1, 2, or 3, $Y^{10}$ is O, S, SO, $SO_2$, NH or $NR^{15}$, or $L^1$ is joined at $Y^{10}$ with $Y^{10}$ being a nitrogen atom;

$R^{15}$ is $C_1$-$C_6$ alkyl optionally substituted with 1-3 $C_1$-$C_6$ alkoxy, hydroxy, amino, and oxo groups, $L^1$- is

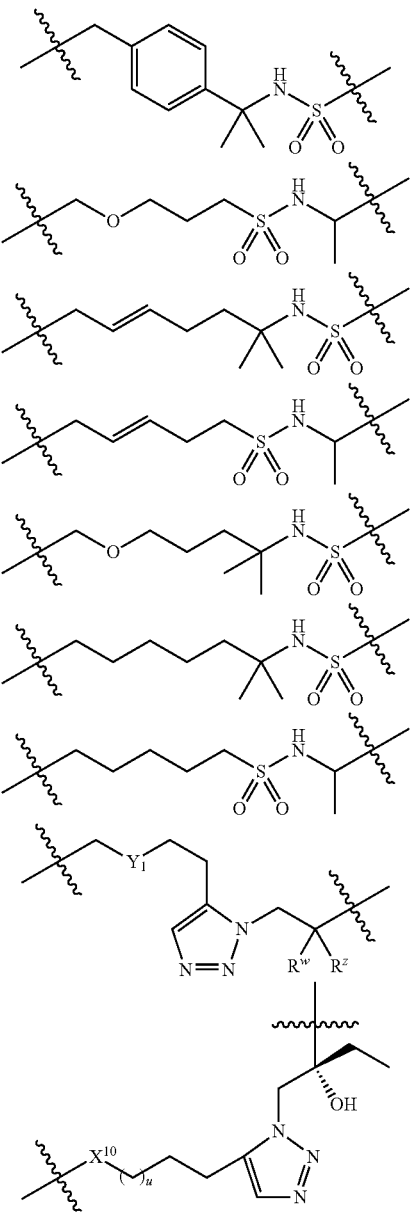

$Y^1$ is $CH_2$, O, S, $X^{10}$ is NH, $NCO_2R^{20}$, O, —CO—, —CO—NH—, or $CH_2$, $R^{20}$ is $C_1$-$C_6$ alkyl optionally substituted with 1-3 $C_6$-$C_{10}$ aryl groups, u is 0, 1, 2, 3, or 4, $R^z$ is hydroxy or hydrogen, $R^w$ is $C_1$-$C_6$ alkyl or hydrogen, and the phenylene and the heteroarylene rings are optionally substituted, Z is phenyl or a 5 or 6 member heteroaryl substituted with an $R^6$ and an $R^{60}$ groups, wherein the $R^6$ and the $R^{60}$ are positioned 1,2 with respect to each other, $R^6$ is hydrogen, optionally substituted $C_1$-$C_6$ alkoxy, or halo, and $R^{60}$ is —$OR^7$ or —$NHR^7R^{70}$, $R^7$ is optionally substituted $C_1$-$C_{10}$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_3$-$C_{10}$ heteroaryl, optionally substituted $C_3$-$C_{10}$ heterocyclyl, or optionally substituted phenyl, and $R^{70}$ is hydrogen or $R^7$.

This disclosure also provides a tautotomer, or its pharmaceutically acceptable salt and/or a solvate of a compound as disclosed herein. Methods to prepare such are known in the art.

This disclosure also provides a stereochemically pure enantiomer of a compound as described herein, its tautotomer, diastereoisomer or its pharmaceutically acceptable salt and/or a solvate thereof. Methods to purify and identify the pure enantiomer are known in the art and described herein.

In another aspect, compositions comprising one or more compounds of the above-noted provided and a carrier are provided herein. In one embodiment, the composition is a pharmaceutical composition and therefore further comprise at least a pharmaceutically acceptable carrier or a pharmaceutically acceptable excipient. The compositions are formulated for various delivery modes, e.g., systemic (oral) or local.

In another aspect, this disclosure provides compositions comprising one or more compounds as provided herein and a dUTPase-directed chemotherapy and a carrier, such as a pharmaceutically acceptable carrier. The compound and chemotherapy can be in varying amounts, and in one aspect, each in an effective amount when used in combination, provides a therapeutic benefit as described herein. The compositions are formulated for various delivery modes, e.g., systemic (oral) or local.

In another aspect, methods are provided for inhibiting deoxyuridine triphosphatase (dUTPase) comprising contacting the dUTPase with an effective amount of a compound or a composition provided herein. In another aspect, the method further comprises contacting the dUTPase with a dUTPase-directed chemotherapy alone or in combination with the compound as provided herein. The contacting can be in vitro, in vivo, simultaneous or concurrent. In a further aspect the dUTPase-directed chemotherapy is contacted prior to the compound or composition as described herein. In another aspect, the dUTPase-directed chemotherapy is contacted subsequent to the compound or composition. In a yet further aspect, the compound or composition and the dUTPase-directed chemotherapy are sequentially administered through several rounds of therapy. The contacting can be simultaneous or concurrent and/or in vitro (cell free), ex vivo or in vivo. In a further aspect, the compounds or compositions of this disclosure are administered to a patient identified or selected for the therapy by determining that the patient has a tumor or mass that over expresses dUTPase. Methods to identify such patients are known in the art and incorporated herein. The methods when administered to a subject such as a human patient, can be first line, second line, third line, fourth line or further therapy.

Also provided is a method for reversing resistance to a dUTPase-directed chemotherapy comprising contacting a cell overexpressing dUTPase with an effective amount of a compound or a composition provided herein, alone or in combination with a dUTPase-directed chemotherapy. In one aspect, the cell is first identified as overexpressing dUTPase by a screen as disclosed by U.S. Pat. No. 5,962,246. In another aspect, the method further comprises subsequently contacting the cell expressing dUTPase with a dUTPase-directed chemotherapy. The methods can be administered as second line, third line, fourth line or further therapy.

Further provided is a method for enhancing the efficacy of a dUTPase-directed chemotherapy comprising contacting a cell, e.g., in one aspect a cell over expressing dUTPase, with an effective amount of a compound or a composition provided herein. In another aspect, the method further comprises contacting the cell with a dUTPase-directed chemotherapy. The contacting can be simultaneous or concurrent and/or in vitro (cell free), ex vivo or in vivo. In a further aspect, the dUTPase-directed chemotherapy is contacted prior to the compound or composition as described herein, or vice versa. The methods when administered to a subject such as a human patient, can be first line, second line, third line, fourth line or further therapy.

In another aspect, provided herein is a method of treating a disease associated with the dUTPase pathway, e.g., cancer, viral infection, bacterial infection, or an autoimmune disorder, comprising administering to a patient in need of such treatment an effective amount of the compound provided herein or a composition provided herein in combination with an agent which is suitable for treating the disease, thereby treating the disease. The administration of the compound of this invention and the agent that is suitable for the disease (e.g., a dUTPase inhibitor) can be simultaneous or concurrent and/or in vitro (cell free), ex vivo or in vivo. In a further aspect the agent that is suitable for treating the disease is administered prior to the compound or composition as described herein, or vice versa. In one aspect, the patient being treated is selected for the therapy by screening a cell or tissue sample isolated from the patient for over expression of dUTPase. The therapy is then administered to this patient after the screen, and the patient has been selected for therapy.

In another aspect, provided herein is a kit comprising a compound provided herein or a composition provided herein. The kit can further comprise one more of a dUTPase inhibitor (e.g., an antitumor agent) and instructions for administering the agent. Yet further provided in the kit are reagents and instructions to screen for dUTPase expression.

In each of the above embodiments, a non-limiting example of the dUTPase mediated chemotherapy comprises a TS-inhibitor, e.g., 5-FU or 5-FU containing therapy such as 5-FU based adjuvant therapy and chemical equivalents thereof.

DETAILED DESCRIPTION

Throughout this disclosure, various publications, patents and published patent specifications are referenced by an identifying citation. The disclosures of these publications, patents and published patent specifications are hereby incorporated by reference into the present disclosure in their entirety to more fully describe the state of the art to which this invention pertains.

Definitions

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2$^{nd}$ edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (R. I. Freshney, ed. (1987)).

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

"Alkenyl" refers to monovalent straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH$($CH_3$)— or —$CH(CH_3)CH_2$—), butylene (—$CH_2CH_2CH_2CH_2$—), isobutylene (—$CH_2CH(CH_3)CH_2$—), sec-butylene (—$CH_2CH_2(CH_3)CH$—), and the like. Similarly, "alkenylene" and "alkynylene" refer to an alkylene moiety containing respective 1 or 2 carbon carbon double bonds or a carbon carbon triple bond.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups, or having from 1-3 carbon atoms replaced with —O—, —S—, or —NR$^Q$— moieties where R$^Q$ is H or $C_1$-$C_6$ alkyl. It is to be noted that when the alkylene is substituted by an oxo group, 2 hydrogens attached to the same carbon of the alkylene group are replaced by "=O". "Substituted alkenylene" and "substituted alkynylene" refer to alkenylene and substituted alkynylene moieties substituted with substituents as described for substituted alkylene.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted awl, heteroaryl, substituted heteroaryl, heterocyclic, and substituted heterocyclic are as defined herein. Acyl includes the "acetyl" group $CH_3C(O)$—.

"Acylamino" refers to the groups —NR$^{47}$C(O)alkyl, —NR$^{47}$C(O) substituted alkyl, —NR$^{47}$C(O)cycloalkyl, —NR$^{47}$C(O) substituted cycloalkyl, —NR$^{47}$C(O)cycloalkenyl, —NR$^{47}$C(O) substituted cycloalkenyl, —NR$^{47}$C(O) alkenyl, —NR$^{47}$C(O) substituted alkenyl, —NR$^{47}$C(O) alkynyl, —NR$^{47}$C(O) substituted alkynyl, —NR$^{47}$C(O)aryl, —NR$^{47}$C(O) substituted aryl, —NR$^{47}$C(O)heteroaryl, —NR$^{47}$C(O) substituted heteroaryl, —NR$^{47}$C(O)heterocyclic, and —NR$^{47}$C(O) substituted heterocyclic wherein R$^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

An animal, subject or patient for diagnosis or treatment refers to an animal such as a mammal, or a human, ovine, bovine, feline, canine, equine, simian, etc. Non-human animals subject to diagnosis or treatment include, for example, simians, murine, such as, rat, mice, canine, leporid, livestock, sport animals, and pets.

"Amino" refers to the group —NH$_2$.

"Substituted amino" refers to the group —NR$^{48}$R$^{49}$ where R$^{48}$ and R$^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R$^{48}$ and R$^{49}$ are optionally joined, together with the nitrogen bound thereto to form a heterocyclic or substituted heterocyclic group, provided that R$^{48}$ and R$^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R$^{48}$ is hydrogen and R$^{49}$ is alkyl, the substituted amino group is sometimes referred to herein as alkylamino. When R$^{48}$ and R$^{49}$ are alkyl, the substituted amino group is sometimes referred to herein as dialkylamino. When referring to a monosubstituted amino, it is meant that either R$^{48}$ or R$^{49}$ is hydrogen but not both. When referring to a disubstituted amino, it is meant that neither R$^{48}$ nor R$^{49}$ are hydrogen.

"Aminocarbonyl" refers to the group —C(O)NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{47}$C(O) NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —$NR^{47}C(S)NR^{50}R^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)$NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —$SO_2NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—$SO_2NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —$NR^{47}SO_2NR^{50}R^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=$NR^{52}$)$NR^{50}R^{51}$ where $R^{50}$, $R^{51}$, and $R^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR$^{47}$C(O)O-alkyl, —NR$^{47}$C(O)O-substituted alkyl, —NR$^{47}$C(O)O-alkenyl, —NR$^{47}$C(O)O-substituted alkenyl, —NR$^{47}$C(O)O-alkynyl, —NR$^{47}$C(O)O-substituted alkynyl, —NR$^{47}$C(O)O-aryl, —NR$^{47}$C(O)O-substituted aryl, —NR$^{47}$C(O)O-cycloalkyl, —NR$^{47}$C(O)O-substituted cycloalkyl, —NR$^{47}$C(O)O-cycloalkenyl, —NR$^{47}$C(O)O-substituted cycloalkenyl, —NR$^{47}$C(O)O-heteroaryl, —NR$^{47}$C(O)O-substituted heteroaryl, —NR$^{47}$C(O)O-heterocyclic, and —NR$^{47}$C(O)O-substituted heterocyclic wherein R$^{47}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

A "composition" as used herein, intends an active agent, such as a compound as disclosed herein and a carrier, inert or active. The carrier can be, without limitation, solid such as a bead or resin, or liquid, such as phosphate buffered saline.

Administration or treatment in "combination" refers to administering two agents such that their pharmacological effects are manifest at the same time. Combination does not require administration at the same time or substantially the same time, although combination can include such administrations.

"Cyano" refers to the group —CN.

"Cycloalkyl" refers to cyclic alkyl groups of from 3 to 10 carbon atoms having single or multiple cyclic rings including fused, bridged, and spiro ring systems. The fused ring can be an aryl ring provided that the non aryl part is joined to the rest of the molecule. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{53}$C(=NR$^{53}$)N(R$^{53}$)$_2$ where each R$^{53}$ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two R$^{53}$ groups attached to a common guanidino nitrogen atom are optionally joined together with the nitrogen bound thereto to form a heterocyclic or substituted heterocyclic group, provided that at least one R$^{53}$ is not hydrogen, and wherein said substituents are as defined herein.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Certain non-limiting examples include pyridinyl, pyrrolyl, indolyl, thiophenyl, oxazolyl, thizolyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazolc, phenoxazine, phenothiazine, imidazolidinc, imidazolinc, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiomorpholinyl), 1,1-dioxothiomorpholinyl, piperidinyl, pyrrolidine, and tetrahydrofuranyl.

"Nitro" refers to the group —NO$_2$.

"Oxo" refers to the atom (=O).

Phenylene refers to a divalent aryl ring, where the ring contains 6 carbon atoms.

Substituted phenylene refers to phenylenes which are substituted with 1 to 4, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-SO$_2$—, phenyl-SO$_2$—, and 4-methylphenyl-SO$_2$—.

"Substituted sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —C(=S)—.

"Thioxo" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Optionally substituted" refers to a group selected from that group and a substituted form of that group. Substituted groups are defined herein. In one embodiment, subtituents are selected from $C_1$-$C_{10}$ or $C_1$-$C_6$ alkyl, $C_2$-$C_6$ alkenyl, $C_2$-$C_6$ alkynyl, $C_6$-$C_{10}$ aryl, $C_3$-$C_8$ cycloalkyl, $C_2$-$C_{10}$ heterocyclyl, $C_1$-$C_{10}$ heteroaryl, halo, nitro, cyano, —$CO_2H$ or a $C_1$-$C_6$ alkyl ester thereof.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring=N— moiety such as pyrazoles, imidazoles, benzimidazoles, triazoles, and tetrazoles.

"Uracil" as referred to herein has the formula:

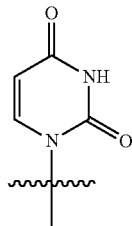 [SMILES: *n1ccc(=O)[nH]c1=O]

"Uracil isostere" refers to an isostere of uracil and does not include uracil or a halouracil. A halouracil, such as 5-fluorouracil or a uracil containing other halogens, are well known to the skilled artisan. Such a moiety provides some or all of the hydrogen bond acceptor-donor-acceptor property of uracil and optionally provides other structural characteristics of uracil. A skilled artisan will further appreciate the meaning of this term by reading the non limiting examples of such uracil isosteres provided herein.

As used herein, the term stereochemically pure denotes a compound which has 80% or greater by weight of the indicated stereoisomer and 20% or less by weight of other stereoisomers. In a further embodiment, the compound of Formula (I), (II), or (III) has 90% or greater by weight of the stated stereoisomer and 10% or less by weight of other stereoisomers. In a yet further embodiment, the compound of Formula (I), (II), or (III) has 95% or greater by weight of the stated stereoisomer and 5% or less by weight of other stereoisomers. In a still further embodiment, the compound of formula (I), (II), or (III) has 97% or greater by weight of the stated stereoisomer and 3% or less by weight of other stereoisomers.

"Pharmaceutically acceptable salt" refers to salts of a compound, which salts are suitable for pharmaceutical use and are derived from a variety of organic and inorganic counter ions well known in the art and include, when the compound contains an acidic functionality, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "Handbook of Pharmaceutically Acceptable Salts," (2002), Verlag Helvetica Chimica Acta, Zürich, Switzerland), for a discussion of pharmaceutical salts, their selection, preparation, and use.

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethancsulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

A solvate of a compound is a solid-form of a compound that crystallizes with less than one, one or more than one molecules of a solvent inside in the crystal lattice. A few examples of solvents that can be used to create solvates, such as pharmaceutically acceptable solvates, include, but are not limited to, water, $C_1$-$C_6$ alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some embodiments, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks. Consistent with this definition and as used herein, the term "therapeutically effective amount" is an amount sufficient to treat a specified disorder or disease or alternatively to obtain a pharmacological response such as inhibiting dUTPase.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

"dUTPase" means any of the following, which are considered to be synonymous, "deoxyuridine triphosphate nucleotidohydrolase", "deoxyuridine triphosphate pyrophosphatase", "dUTP nucleotidohydrolase", "dUTP pyrophosphatase", and other equivalent nomenclature for the dUTPase enzyme. In one aspect, dUTPase intends DUT-N and DUT-M. In other aspects, it is DUT-N only, or alternatively, DUT-M only. The amino acid and coding sequences for dUTPase are known in the art and disclosed in U.S. Pat. No. 5,962,246. Methods for expressing and screening for expression level of the enzyme are disclosed in U.S. Pat. No. 5,962,246 and Ladner et al. (US Patent Publ. No. 2011/0212467A1).

"DUT-N" means the nuclear form of dUTPase.

"DUT-M" means the mitochondrial or cytoplasmic form of dUTPase.

"dUTPase-directed therapy" intends therapeutics that target the dUTPase pathway, e.g., in the case of cancer, e.g. TS-directed therapies and the fluoropyrimidines (such as 5-FU), pemetrexed (Alimta®), capecitabine (Xcloda®), S-1 and antifolates (such as methotrexate) and chemical equivalents thereof. Non-limiting examples include 5-flurouracil (5-FU), TS-directed therapies and 5-FU based adjuvant therapy. Combination therapies can include any intervention that alters nucleotide pools and/or sensitizes the immune cells or viruses to the dUTPase inhibitor, as are well known to the skilled artisan. For rheumatoid arthritis, for example, the combination can be with an dihydrofolate reductase (DHFR) inhibitor such as methotrexate.

5-fluorouracil (5-FU) belongs to the family of therapy drugs called pyrimidine based anti-metabolites. It is a pyrimidine analog, which is transformed into different cytotoxic metabolites that are then incorporated into DNA and RNA thereby inducing cell cycle arrest and apoptosis. Chemical equivalents are pyrimidine analogs which result in disruption of DNA replication. Chemical equivalents inhibit cell cycle progression at S phase resulting in the disruption of cell cycle and consequently apoptosis. Equivalents to 5-FU include prodrugs, analogs and derivative thereof such as 5'-deoxy-5-fluorouridine (doxifluoroidine), 1-tetrahydrofuranyl-5-fluorouracil (ftorafur), capecitabine (Xeloda®), S-1 (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487.

"5-FU based adjuvant therapy" refers to 5-FU alone or alternatively the combination of 5-FU with other treatments, that include, but are not limited to radiation, methyl-CCNU, leucovorin, oxaliplatin, irinotecin, mitomycin, cytarabine, levamisole. Specific treatment adjuvant regimens are known in the art as FOLFOX, FOLFOX4, FOLFIRI, MOF (semustine (methyl-CCNU), vincrisine (Oncovin®) and 5-FU). For a review of these therapies see Beaven and Goldberg (2006) Oncology 20(5):461-470. An example of such is an effective amount of 5-FU and Leucovorin. Other chemotherapeutics can be added, e.g., oxaliplatin or irinote can.

Capecitabine is a prodrug of (5-FU) that is converted to its active form by the tumor-specific enzyme PynPase following a pathway of three enzymatic steps and two intermediary metabolites, 5'-deoxy-5-fluorocytidine (5'-DFCR) and 5'-deoxy-5-fluorouridine (5'-DFUR). Capecitabine is marketed by Roche under the trade name Xeloda®.

Leucovorin (Folinic acid) is an adjuvant used in cancer therapy. It is used in synergistic combination with 5-FU to improve efficacy of the chemotherapeutic agent. Without being bound by theory, addition of Leucovorin is believed to enhance efficacy of 5-FU by inhibiting thymidylate synthase. It has been used as an antidote to protect normal cells from high doses of the anticancer drug methotrexate and to increase the antitumor effects of fluorouracil (5-FU) and tegafur-uracil. It is also known as citrovorum factor and Wellcovorin. This compound has the chemical designation of L-Glutamic acid N[4[[(2-amino-5-formyl1,4,5,6,7,8hexahydro4oxo6-pteridinyl)methyl]amino]b-enoyl], calcium salt (1:1).

"Oxaliplatin" (Eloxatin) is a platinum-based chemotherapy drug in the same family as cisplatin and carboplatin. It is typically administered in combination with fluorouracil and leucovorin in a combination known as FOLFOX for the treatment of colorectal cancer. Compared to cisplatin, the two amine groups are replaced by cyclohexyldiamine for improved antitumour activity. The chlorine ligands are replaced by the oxalato bidentate derived from oxalic acid in order to improve water solubility. Equivalents to Oxaliplatin are known in the art and include, but are not limited to cisplatin, carboplatin, aroplatin, lobaplatin, nedaplatin, and JM-216 (see McKeage et al. (1997) J. Clin. Oncol. 201:

1232-1237 and in general, Chemotherapy for Gynecological Neoplasm, Curr. Therapy and Novel Approaches, in the Series Basic and Clinical Oncology, Angioli et al. Eds., 2004).

"FOLFOX" is an abbreviation for a type of combination therapy that is used to treat cancer. This therapy includes 5-FU, oxaliplatin and leucovorin. "FOLFIRI" is an abbreviation for a type of combination therapy that is used treat cancer and comprises, or alternatively consists essentially of, or yet further consists of 5-FU, leucovorin, and irinotecan. Information regarding these treatments are available on the National Cancer Institute's web site, cancer.gov, last accessed on Jan. 16, 2008.

Irinotecan (CPT-11) is sold under the trade name of Camptosar. It is a semi-synthetic analogue of the alkaloid camptothecin, which is activated by hydrolysis to SN-38 and targets topoisomerase I. Chemical equivalents are those that inhibit the interaction of topoisomerase I and DNA to form a catalytically active topoisomerase I-DNA complex. Chemical equivalents inhibit cell cycle progression at G2-M phase resulting in the disruption of cell proliferation.

The term "adjuvant" therapy refers to administration of a therapy or chemotherapeutic regimen to a patient after removal of a tumor by surgery. Adjuvant therapy is typically given to minimize or prevent a possible cancer reoccurrence. Alternatively, "neoadjuvant" therapy refers to administration of therapy or chemotherapeutic regimen before surgery, typically in an attempt to shrink the tumor prior to a surgical procedure to minimize the extent of tissue removed during the procedure.

The phrase "first line" or "second line" or "third line" etc., refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as primary therapy and primary treatment." See National Cancer Institute website as www.cancer.gov, last visited on May 1, 2008. Typically, a patient is given a subsequent chemotherapy regimen because the patient did not shown a positive clinical or sub-clinical response to the first line therapy or the first line therapy has stopped.

As used herein, the term "antifolate" intends a drug or biologic that impairs the function of folic acids, e.g., an antimetabolite agent that inhibits the use of a metabolite, i.e. another chemical that is part of normal metabolism. In cancer treatment, antimetabolites interfere with DNA production, thus cell division and growth of the tumor. Non-limiting examples of these agents are dihydrofolate reductase inhibitors, such as methotrexate, Aminopterin, and Pemetrexed; thymidylate synthase inhibitors, such as Raltitrexed or Pemetrexed; purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU).

In one aspect, the term "chemical equivalent" means the ability of the chemical to selectively interact with its target protein, DNA, RNA or fragment thereof as measured by the inactivation of the target protein, incorporation of the chemical into the DNA or RNA or other suitable methods. Chemical equivalents include, but are not limited to, those agents with the same or similar biological activity and include, without limitation a pharmaceutically acceptable salt, and/or a solvate thereof, or mixtures thereof that interact with and/or inactivate the same target protein, DNA, or RNA as the reference chemical.

The terms "oligonucleotide" or "polynucleotide" or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

When a genetic marker, e.g., over expression of dUTPase, is used as a basis for selecting a patient for a treatment described herein, the genetic marker is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one in the art, measurement of the genetic marker in a clinical setting is a clear indication that this parameter was used as a basis for initiating, continuing, adjusting and/or ceasing administration of the treatments described herein.

"Cancer" is a known medically as a malignant neoplasm, is a broad group of diseases involving unregulated cell growth. In cancer, cells divide and grow uncontrollably, forming malignant tumors, and invade nearby parts of the body. Non-limiting examples include colon cancer, colorectal cancer, gastric cancer, esophogeal cancer, head and neck cancer, breast cancer, lung cancer, stomach cancer, liver cancer, gall bladder cancer, or pancreatic cancer or leukemia.

The following are non-limiting aspects of the present disclosure.

Compounds

In one embodiment, provided herein is a compound of Formula (I), which is of Formula (III):

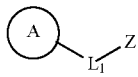

wherein A is an uracil isostere of formula:

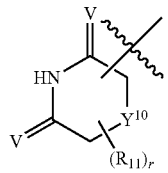

each V is independently O or S,
R$^{11}$ is hydrogen, halo, R$^{12}$ or —O—R$^{12}$, wherein R$^{12}$ is C$_1$-C$_6$ alkyl, C$_2$-C$_6$ alkenyl, or C$_2$-C$_6$ alkynyl optionally substituted with 1-3 hydroxy, fluoro, chloro, and amino substituent,
r is 1, 2, or 3,
Y$^{10}$ is O, S, SO, SO$_2$, NH or NR$^{15}$, or L$^1$ is joined at Y$^{10}$ with Y$^{10}$ being a nitrogen atom;
R$^{15}$ is C$_1$-C$_6$ alkyl optionally substituted with 1-3 C alkoxy, hydroxy, amino, and oxo groups,
L$^1$- is

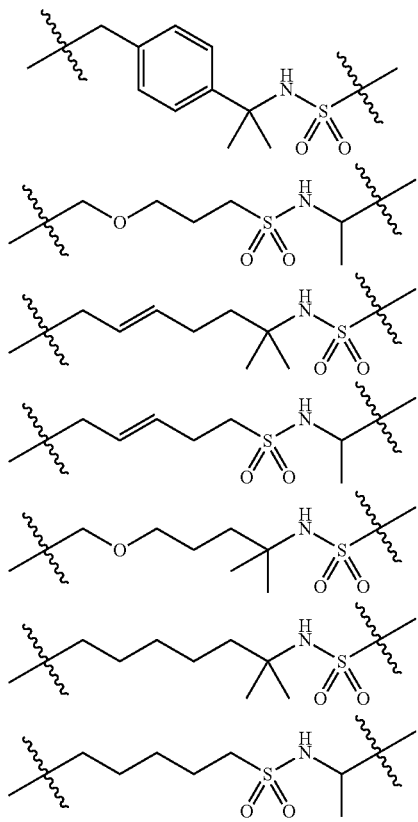

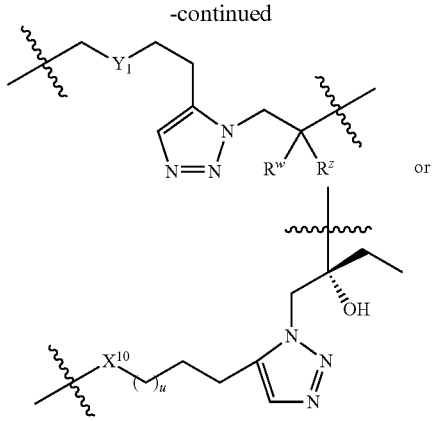

Y$^1$ is CH$_2$, O, S,
X$^{10}$ is NH, NCO$_2$R$^{20}$, O, —CO—, —CO—NH—, or CH$_2$,
R$^{20}$ is C$_1$-C$_6$alkyl optionally substituted with 1-3 C$_6$-C$_{10}$ aryl groups,
u is 0, 1, 2, 3, or 4,
R$^z$ is hydroxy or hydrogen,
R$^w$ is C$_1$-C$_6$ alkyl or hydrogen, and
the phenylene and the heteroarylene rings are optionally substituted,
Z is phenyl or a 5 or 6 member heteroaryl substituted with an R$^6$ and an R$^{60}$ groups, wherein the R$^6$ and the R$^{60}$ are positioned 1,2 with respect to each other,
R$^6$ is hydrogen, optionally substituted C$_1$-C$_6$ alkoxy, or halo, and
R$^{60}$ is —OR$^7$ or —NHR$^7$R$^{70}$,
R$^7$ is optionally substituted C$_1$-C$_{10}$ alkyl, optionally substituted C$_2$-C$_6$ alkenyl, optionally substituted C$_2$-C$_6$ alkynyl, optionally substituted C$_3$-C$_8$ cycloalkyl, optionally substituted C$_3$-C$_{10}$ heteroaryl, optionally substituted C$_3$-C$_{10}$ heterocyclyl, or optionally substituted phenyl, and
R$^{70}$ is hydrogen or R$^7$.

In one embodiment, each V is O. In another embodiment, each V is S. In another embodiment, X$^{10}$ is NH. In another embodiment, X$^{10}$ is NCO$_2$R$^{20}$. In another embodiment, X$^{10}$ is O. In another embodiment, X$^{10}$ is —CO—. In another embodiment, X$^{10}$ is —CO—NH—. In another embodiment, X$^{10}$ is CH$_2$.

In another embodiment, the uracil isostere is:

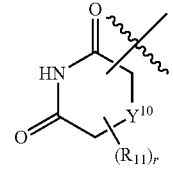

wherein Y$^{10}$ is O, S, SO, SO$_2$, NH or NR$^{15}$.

In some embodiments, the uracil isostere is:

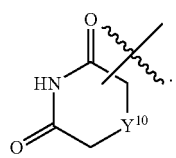

In another embodiment, $Y^{10}$ is O. In another embodiment, $Y^{10}$ is NH.

In some embodiments, the uracil isostere is:

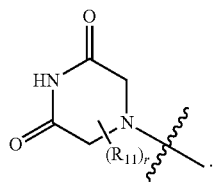

In another embodiment, $R^{11}$ is hydrogen. In another embodiment, $R^{11}$ is $C_1$-$C_6$ alkyl, $C_2$-$C_6$ alkenyl, or $C_2$-$C_6$ alkynyl optionally substituted with 1-3 hydroxy, fluoro, chloro, and amino substituent. In another embodiment, $R^{11}$ is methyl. In another embodiment, $R^1$ is a non-hydrogen substituent, and r is 1. In another embodiment, $R^1$ is a non-hydrogen substituent, and r is 2. In another embodiment, $R^1$ is a non-hydrogen substituent, and r is 3.

In another embodiment, —W—X—Y— is —CH$_2$—X—SO$_2$—NH—CH(R$^Y$)—; —CH$_2$—X—SO$_2$—NH—C(R$^Y$)$_2$—; or —CH$_2$—X—B—CH$_2$CR$^X$R$^W$—, X is optionally substituted $C_1$-$C_6$ alkylene wherein one of the methylene groups within the alkylene chain is optionally replaced with an O or S atom, such that X is optionally substituted alkylene or optionally substituted heteroalkylene;
B is a optionally substituted $C_3$-$C_{10}$ heteroaryl;
R$^Y$ an R$^W$ are independently hydrogen or $C_1$-$C_6$ alkyl; and
R$^z$ is hydrogen or hydroxy.

In one embodiment, B is a 5 membered heteroaryl containing up to 3 or 4 heteroatoms selected from nitrogen, sulfur and oxygen. In one embodiment, B is:

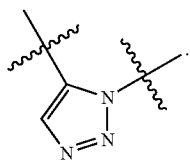 [SMILES: *c1cnnn1*]

In another embodiment, —W—X—Y— or $L^1$ is

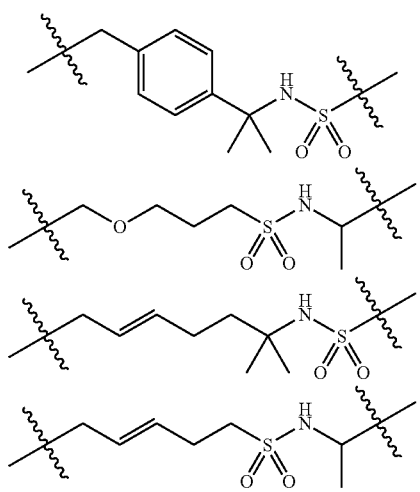

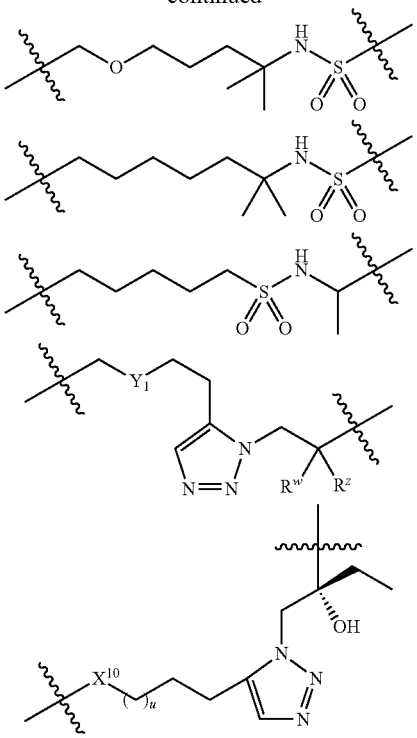

$Y^1$ is CH$_2$, O or S,
$X^{10}$ and u are as defined herein,
R$^z$ is hydroxy or hydrogen,
R$^w$ is $C_1$-$C_6$ alkyl or hydrogen,
the phenylene and the heteroarylene rings are optionally substituted.

In some embodiments, —W—X—Y— or $L^1$ is

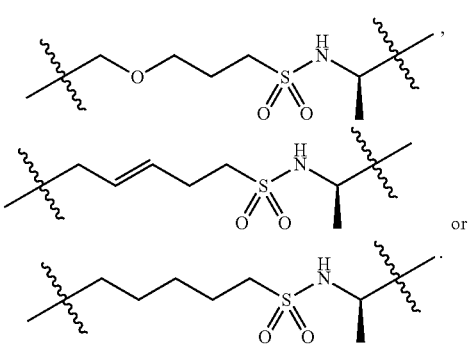

In some embodiments, —W—X—Y— or $L^1$ is

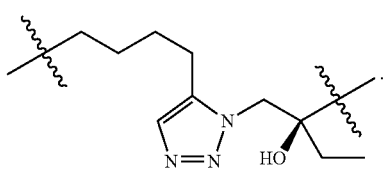 [SMILES: *CCCCc1cnnn1C[C@@](*)(O)CC]

In another embodiment, $R^4$ is optionally substituted $C_6$-$C_{10}$ aryl. In another embodiment, $R^4$ is optionally substituted $C_2$-$C_{10}$ heterocyclic group. In another embodiment, $R^4$ is optionally substituted $C_1$-$C_{10}$ heteroaryl group. In another embodiment, when Y is -$L^{10}$-$B^1$-$L^{11}$-, Z is $R^4$.

In some embodiments, Z is phenyl or a 5 or 6 membered heteroaryl substituted with an $R^6$ and an $R^{60}$ groups, wherein the $R^6$ and the $R^{60}$ are positioned 1,2 with respect to each other,
$R^6$ is hydrogen, optionally substituted $C_1$-$C_6$ alkoxy, or halo,
$R^{60}$ is —$OR^7$ or —$NHR^7R^{70}$,
$R^7$ is optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_3$-$C_{10}$ heteroaryl, optionally substituted $C_3$-$C_{10}$ heterocyclyl, or optionally substituted phenyl, and
$R^{70}$ is hydrogen or $R^7$.

In some embodiments, Z or $R^4$ is selected from:

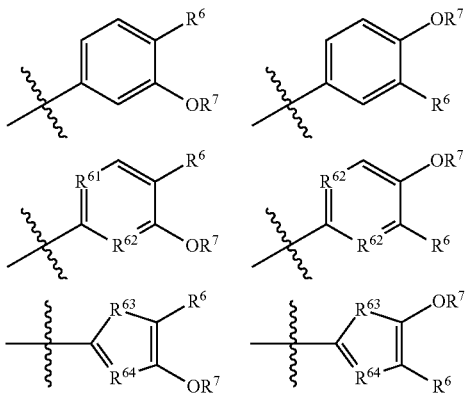

wherein each $R^6$ and $R^7$ independently are defined as in any aspect or embodiment above,
each $R^{61}$ and $R^{62}$ independently is N or CH, provided that at least one of $R^{61}$ and $R^{62}$ is N,
each $R^{63}$ independently is $NR^{70}$, S, O, and
each $R^{64}$ independently is N or CH.

In some embodiments, provided herein is a compound of formula:

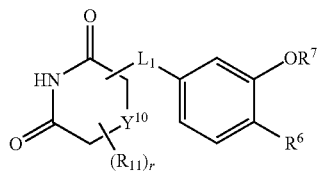

wherein the variables are as defined herein.

In some embodiments, provided herein is a compound of formula:

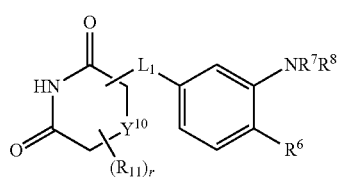

wherein the variables are as defined herein, and $R^8$ is defined as $R^7$, independently of each other.

In another embodiment, Z is:

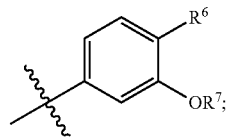

$R^6$ is hydrogen, optionally substituted $C_1$-$C_6$ alkoxy, or halo, and
$R^7$ is optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_3$-$C_{10}$ heteroaryl, optionally substituted $C_3$-$C_{10}$ heterocyclyl, or optionally substituted phenyl.

In one embodiment, $R^6$ is hydrogen. In one embodiment, $R^6$ is halo. In another embodiment, $R^6$ is fluoro. In one embodiment, $R^6$ is $C_1$-$C_6$ alkoxy. In one embodiment, $R^6$ is $C_1$-$C_6$ alkoxy substituted with 1-3 fluoro groups. In some embodiments, $R^6$ is hydrogen, F, Cl, OMe, or $OCF_3$.

In one embodiment, $R^7$ is $C_1$-$C_6$ alkyl substituted with a $C_3$-$C_8$ cycloalkyl, $C_2$-$C_{10}$ heterocyclyl, or $C_1$-$C_{10}$ heteroaryl. In one embodiment, $R^7$ is

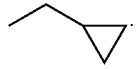

In one embodiment, $R_7$ is $C_1$-$C_6$ alkyl optionally substituted with a $C_3$-$C_8$ cycloalkyl, 4-8 membered heterocyclyl, or $R^7$ is $C_1$-$C_6$ alkyl substitute with 1-3 fluoro atoms.

In another embodiment, $R^7$ is:

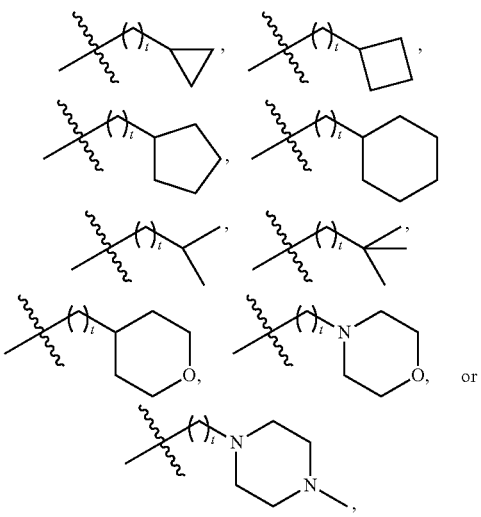

wherein t is 1, 2, or 3. In another embodiment, t is 1. In another embodiment, t is 2. In another embodiment, t is 3.

In another embodiment, the cycloalkyl is cyclopropyl. In another embodiment, the cycloalkyl is cyclobutyl. In another embodiment, the cycloalkyl is cyclopentyl. In another embodiment, the cycloalkyl is cyclohexyl. In another embodiment, $R^7$ is isobutyl. In another embodiment, $R^7$ is neopentyl.

In another embodiment, the heterocyclyl is

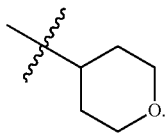 [SMILES: *C1CCOCC1]

In another embodiment, the heterocyclyl is:

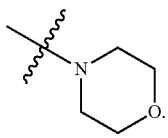 [SMILES: *N1CCOCC1]

In another embodiment, the heterocyclyl is:

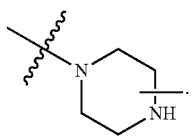

In another embodiment, the compound is of formula:

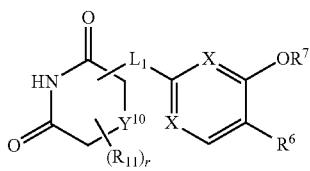

wherein $L_1$ is defined as above.

In another embodiment, the compound is of formula:

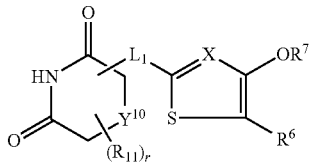

wherein $L_1$ is defined as above.

In another embodiment, the compound is of formula:

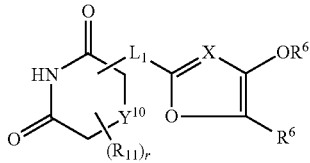

wherein $L_1$ is defined as above.

In another embodiment, the compound is of formula:

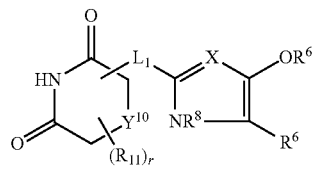

wherein $L_1$ is defined as above.

In one embodiment, provided herein is a compound of formula:

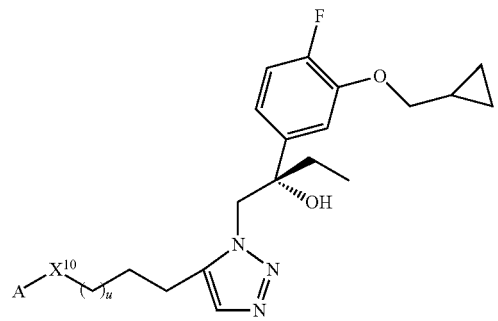

wherein A is selected from:

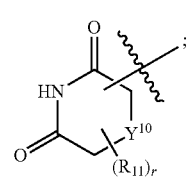

wherein $Y^{10}$, $R^{11}$ and r are as defined herein;

$X^{10}$ is NH, $NCO_2R^{20}$, O, —CO—NH—, or $CH_2$;

$R^{20}$ is $C_1$-$C_6$ alkyl optionally substituted with 1-3 $C_6$-$C_{10}$ aryl groups;

u is 0, 1, 2, 3, or 4;

$R^{11}$ is hydrogen, $C_1$-$C_6$ alkyl, $C_2$-$C_6$ alkenyl, or $C_2$-$C_6$ alkynyl wherein each alkyl, alkenyl, and alkynyl is optionally substituted with 1-3 hydroxy, fluoro, chloro, and amino substituent; and r is 1 or 2.

In another embodiment, $X^{10}$ is $CH_2$. In another embodiment, $X^{10}$ is NH. In another embodiment, $X^{10}$ is —CO—NH—. In another embodiment, u is 1. In another embodiment, u is 2. In another embodiment, u is 3.

In another embodiment, provided herein is a compound selected from:

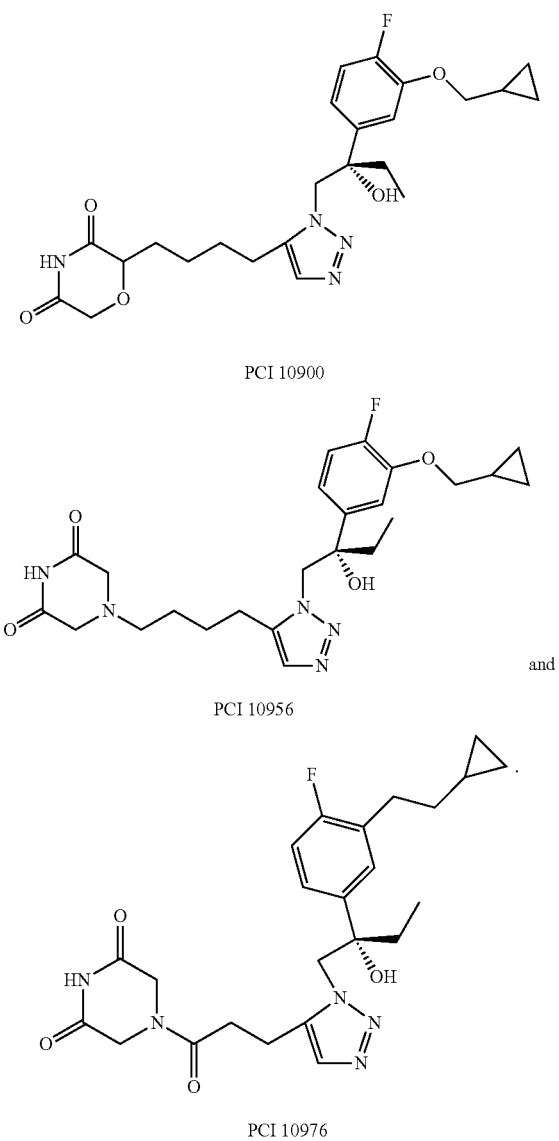

PCI 10900

PCI 10956 and

PCI 10976 and a diastereomer or an enantiomer thereof.

The compounds provided herein include individual, separated enantiomers and diastereomers that are stereochemically pure or enriched, tautotomers, and pharmaceutically acceptable salts, and/or a solvate thereof, wherever applicable. As used herein, the term stereochemically pure denotes a compound which has 80% or greater by weight of the indicated stereoisomer and 20% or less by weight of other stereoisomers. In a further aspect, the compounds as described herein have 90% or greater by weight of the denoted stereoisomer and 10% or less by weight of other stereoisomers. In a yet further embodiment, the compounds of this disclosure have 95% or greater by weight of the denoted stereoisomer and 5% or less by weight of other stereoisomers. In a still further embodiment, the compounds have 97% or greater by weight of the denoted stereoisomer and 3% or less by weight of other stereoisomers. Any one or more of the compounds can be provided as compositions, e.g., of pharmaceutically acceptable salt, and/or a solvate thereof.

Synthesis

The following general synthetic scheme is used to prepare the compounds provided herein. For example, compounds of formula I are synthesized as shown in the reaction scheme below:

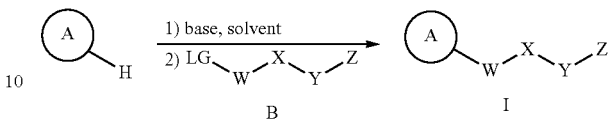

wherein A, X—Y—, $L_1$, and Z are as defined herein, and H is hydrogen. In general, uracil, uracil isostere, or a halo uracil is treated with a suitable base such as butyl lithium in a solvent such as tetrahydrofuran or dimethylformamide. The A(-) anion obtained by deprotonation of the A-H moiety and also by halogen exchange of an A-halo bond with an alkyl lithium. It is then coupled with compound B, wherein LG is a leaving group such as halogen, tosylate or mesylate to provide compounds of formula (I). In some embodiments, protection of an NH, OH, or such other group in uracil, uracil isostere, halo uracil, or the —W—X—Y—Z moiety is required. Compounds of formula (III) can also be synthesized in an analogous manner. An uracil isostere containing an —NH— or an $NH_2$ group can also be alkylated following reductive amination as is well known to a skilled artisan.

A-ring substituted compounds provided here are synthesized as shown below and or following methods well known in the art in view of the present disclosure. See also, Journal of Heterocyclic Chemistry (2005) vol. 42, #2 p. 201-207, Journal of the American Chemical Society (2009) vol. 131, p. 8196-8210, Journal of Heterocyclic Chemistry (1994) vol. 31, #2 p. 565-568, and Journal of Medicinal Chemistry (1994) vol. 37, #13 p. 2059-2070, each of which is incorporated herein by reference.

Additional —W—X—Y—Z moieties are disclosed in US 2011/0082163; US 2012/0225838; Miyahara et al., J. Med. Chem. (2012) 55, 2970-2980; Miyakoshi et al., J. Med. Chem. (2012) 55, 2960-2969; Miyahara et al., J. Med. Chem. (2012) 55 (11), pp 5483-5496; and Miyakoshi et al., J. Med. Chem. (2012) 55 (14), pp 6427-6437 (each of which are incorporated herein by reference) and can be used with the A moieties disclosed herein.

These and other compounds provided herein are synthesized following art recognized methods with the appropriate substitution of commercially available reagents as needed. For example, and without limitation, methods for synthesizing certain other compounds are described in US 2011/0082163; US 2012/0225838; Miyahara et al., J. Med. Chem. (2012) 55, 2970-2980; Miyakoshi et al., J. Med. Chem. (2012) 55, 2960-2969; Miyahara et al., J. Med. Chem. (2012) 55 (11), pp 5483-5496; and Miyakoshi et al., J. Med. Chem. (2012) 55 (14), pp 6427-6437 (each supra), which methods can be adapted by the skilled artisan upon reading this disclosure and/or based on synthetic methods well known in the art, to prepare the compounds provided herein. Protection deprotection methods and protecting groups useful for such purposes are well known in the art, for example in Greene's Protective Groups in Organic Synthesis, $4^{th}$ Edition, Wiley, 2006, or a later edition of the book.

The compounds and the intermediates are separated from the reaction mixture, when desired, following art known methods such as crystallization, chromatography, distillation, and the like. The compounds and the intermediates are characterized by art known methods such as thin layer chromatography, nuclear magnetic resonance spectroscopy, high performance liquid chromatography, and the like. As described in detail herein, a racemic or diastereomeric mixture of the compound can be separated or enriched to the enantiomers and diastereomers and tested and used diagnostically or therapeutically as described herein.

Methods of testing and using the compounds provided herein are performed following art recognized in vitro (cell free), ex vivo or in vivo methods. For example, and without limitation, certain methods for testing and using other compounds are described in US 2011/0082163; US 2012/0225838; Miyahara et al., J. Med. Chem. (2012) 55, 2970-2980; Miyakoshi et al., J. Med. Chem. (2012) 55, 2960-2969; Miyahara et al., J. Med. Chem. (2012) 55 (11), pp 5483-5496; Miyakoshi et al., J. Med. Chem. (2012) 55 (14), pp 6427-6437 (each of which in incorporated by reference), which methods can be adapted by the skilled artisan upon reading this disclosure and/or based on methods well known in the art, to test and use the compounds provided herein.

Compositions

Compositions, including pharmaceutical compositions comprising the compounds described herein can be manufactured by means of conventional mixing, dissolving, granulating, dragee-making levigating, emulsifying, encapsulating, entrapping, or lyophilization processes. The compositions can be formulated in conventional manner using one or more physiologically acceptable carriers, diluents, excipients, or auxiliaries which facilitate processing of the compounds provided herein into preparations which can be used pharmaceutically.

The compounds of the technology can be administered by parenteral (e.g., intramuscular, intraperitoneal, intravenous, ICV, intracisternal injection or infusion, subcutaneous injection, or implant), oral, by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration.

In one embodiment, this disclosure relates to a composition comprising a compound as described herein and a carrier.

In another embodiment, this disclosure relates to a pharmaceutical composition comprising a compound as described herein and a pharmaceutically acceptable carrier.

In another embodiment, this disclosure relates to a pharmaceutical composition comprising a therapeutically effective amount of a compound as described herein and a pharmaceutically acceptable carrier.

The pharmaceutical compositions for the administration of the compounds can be conveniently presented in dosage unit form and can be prepared by any of the methods well known in the art of pharmacy. The pharmaceutical compositions can be, for example, prepared by uniformly and intimately bringing the compounds provided herein into association with a liquid carrier, a finely divided solid carrier or both, and then, if necessary, shaping the product into the desired formulation. In the pharmaceutical composition the compound provided herein is included in an amount sufficient to produce the desired therapeutic effect. For example, pharmaceutical compositions of this disclsoure may take a form suitable for virtually any mode of administration, including, for example, topical, ocular, oral, buccal, systemic, nasal, injection, infusion, transdermal, rectal, and vaginal, or a form suitable for administration by inhalation or insufflation.

For topical administration, the compounds can be foiuiulated as solutions, gels, ointments, creams, suspensions, etc., as is well-known in the art.

Systemic formulations include those designed for administration by injection (e.g., subcutaneous, intravenous, infusion, intramuscular, intrathecal, or intraperitoneal injection) as well as those designed for transdermal, transmucosal, oral, or pulmonary administration.

Useful injectable preparations include sterile suspensions, solutions, or emulsions of the compounds provided herein in aqueous or oily vehicles. The compositions may also contain formulating agents, such as suspending, stabilizing, and/or dispersing agents. The formulations for injection can be presented in unit dosage form, e.g., in ampules or in multidose containers, and may contain added preservatives.

Alternatively, the injectable formulation can be provided in powder form for reconstitution with a suitable vehicle, including but not limited to sterile pyrogen free water, buffer, and dextrose solution, before use. To this end, the compounds provided herein can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets, or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets can be coated by methods well known in the art with, for example, sugars, films, or enteric coatings.

Compositions intended for oral use can be prepared according to any method known to the art for the manufacture of pharmaceutical compositions, and such compositions may contain one or more agents selected from the group consisting of sweetening agents, flavoring agents, coloring agents, and preserving agents in order to provide pharmaceutically elegant and palatable preparations. Tablets contain the compounds provided herein in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch or alginic acid); binding agents (e.g. starch, gelatin, or acacia); and lubricating agents (e.g., magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques well known to the skilled artisan. The pharmaceutical compositions of the technology may also be in the form of oil-in-water emulsions.

Liquid preparations for oral administration may take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin, or acacia); non-aqueous vehicles (e.g., almond oil, oily esters, ethyl alcohol, Cremophore™, or fractionated vegetable oils); and preservatives (e.g., methyl or propyl-p-hydroxybenzoates or sorbic acid). The preparations may also contain buffer salts, preservatives, flavoring, coloring, and sweetening agents as appropriate.

Use of Compounds for Preparing Medicaments

The compounds and compositions of the present invention are also useful in the preparation of medicaments to treat a variety of pathologies as described herein. The methods and techniques for preparing medicaments of a composition are known in the art. For the purpose of illustration only, pharmaceutical formulations and routes of delivery are detailed herein.

Thus, one of skill in the art would readily appreciate that any one or more of the compositions described above, including the many specific embodiments, can be used by applying standard pharmaceutical manufacturing procedures to prepare medicaments to treat the many disorders described herein. Such medicaments can be delivered to the subject by using delivery methods known in the pharmaceutical arts.

Methods and Therapies

The compositions and compounds as disclosed herein are useful in methods of inhibiting dUTPase or enhancing the efficacy of a dUTPase-directed therapy, or yet further, reversing resistance to dUTPase therapies. The methods comprise, or alternatively consist essentially of, or yet further consist of, contacting the dUTPase with an effective amount of the compound or composition as disclosed herein. In one embodiment, the methods further comprise, or alternatively consist essentially of, or yet further consist of, contacting the dUTPase with an effective amount of a dUTPase-directed therapy. In one aspect, the contacting of the dUTPase-directed therapy is prior to, concurrent or subsequent to contacting with the compound or composition of this disclosure.

One of skill in the art can also determine if the compound or combination inhibits dUTPase in vitro by contacting the compound or combination with purified or recombinant dUTPase in a cell free system. The purified or recombinant dUTPase and can be from any species, e.g., simian, canine, bovine, ovine, rat, mouse or human. In one aspect, the dUTPase is DUT-N or DUT-M. Isolation, characterization and expression of dUTPase isoforms are disclosed in U.S. Pat. No. 5,962,246 and known in the art.

The contacting can be performed cell-free in vitro or ex vivo with a cell or in a cell culture. When performed in vitro or ex vivo, the compounds, compositions or agents can be directly added to the enzyme solution or added to the cell culture medium. When practiced in vitro or ex vivo, the method can be used to screen for novel combination therapies, formulations or treatment regimens, prior to administration to administration to an animal or a human patient. Methods to quantify inhibition are known in the art, see, U.S. Patent Publ. Nos. 2010/0075924 and 2011/0212467 and U.S. Pat. No. 7,601,702. For example, a fixed dose of a dUTPase directed therapy (e.g., 5-FU or Pemetrexed) can be added to the system and varying amounts of the compound can be subsequently added to system. Alternatively, a fixed dose of a compound of this invention can be added to the system and varying amounts of the dUTPase directed therapy (e.g., 5-FU or Pemetrexed) compound can be subsequently added to system.

In one aspect, the contacting is ex vivo and the cell or tissue to be contacted over expresses dUTPase. These cells can be isolated from a patient prior to administration to the patient or can be purchased from a depository such as the American Type Culture Collection (ATCC). Non-limiting examples of animal (e.g., canine, an equine, a bovine, a feline, an ovine, a mouse, a rat or a simian) and human cells that are known to over express dUTPase include, without limitation cancer cells, e.g. colon cancer, colorectal cancer, gastric cancer, head and neck cancer, breast cancer, stomach cancer or lung cancer. The cancer can be metastatic or non-metastatic. Methods to quantify inhibition are known in the art, see, U.S. Patent Publ. Nos. 2010/0075924 and 2011/0212467 and U.S. Pat. No. 7,601,702 and Wilson et al. (2012) Mol. Cancer Ther. 11:616-628.

When practiced in vivo in a patient such as an animal or human, the compounds, compositions or agents are administered in an effective amount by a suitable route of administration, as determined by a treating physician taking into account the patient, disease and other factors. When practiced in a non-human animal, e.g., an appropriate mouse model, the method can be used to screen for novel combination therapies, formulations or treatment regimens, prior to administration to a human patient.

This disclosure also provides methods of treating a disease whose treatment is impeded by the expression of dUTPase, comprising, or alternatively consisting essentially of, or yet further consisting of, administering to a patient in need of such treatment an effective amount of the compound or composition of this disclosure, thereby treating the disease. In one aspect, the method further comprises isolating a cell or tissue sample from the patient and screening for the expression level of dUTPase, wherein over expression of dUTPase in the sample as compared to a control sample serves as a basis for selecting the patient as suitable for the method and therapies. Methods to quantify dUTPase are known in the art. Effective amounts will vary with the patient, the disease and the general health of the patient and are determined by the treating physician. Methods to quantify inhibition are known in the art, see, U.S. Patent Publ. Nos. 2010/0075924 and 2011/0212467 and U.S. Pat. No. 7,601,702 and Wilson et al. (2012) Mol. Cancer Ther. 11:616-628. If the patient sample shows over expression of dUTPase, the therapy is administered to the patient. If the patient sample does not show over expression, an alternate therapy is chosen. The screen can be repeated throughout therapy as a means to monitor the therapy and/or dosage regimen.

To practice this method, the sample is a patient sample containing the tumor tissue, normal tissue adjacent to said tumor, normal tissue distal to said tumor or peripheral blood lymphocytes. In a further aspect, the patient or patient population to be treated also is treatment naïve.

In one aspect, the method also requires isolating a sample containing the marker from the patient to be treated. It is conceivable that one of skill in the art will be able to analyze and identify markers in situ at some point in the future. Accordingly, in one aspect, the inventions of this application are not to be limited to requiring isolation of the patient sample prior to analysis.

These methods also are not limited by the technique that is used to identify the expression level of dUTPase or other relevant enzyme or markers. Suitable methods include but are not limited to the use of hybridization probes, antibodies, primers for PCR analysis, and gene chips, slides and software for high throughput analysis. Additional markers can be assayed and used as negative controls.

In one aspect, the subject or patient is an animal or a human patient. Non-limiting examples of animals include a feline, a canine, a bovine, an equine, an ovine, a mouse, a rat or a simian.

Diseases in which treatment is impeded by the expression of dUTPase include, without limitation, cancer, viral infection, bacterial infection or an autoimmune disorder. For example, in rheumatoid arthritis, inflammatory bowel disease or other autoimmune disorders, a dUTPase inhibitor can be used in combination with an antifolate or fluoropyrimidine or other thymidylate synthase and dihydrofolate reductase inhibitors; parasitic, viral or bacterial infections can be treated similarly employing a combination therapy including a dUTPase inhibitor. Non-limiting examples of cancer include, colon cancer, colorectal cancer, gastric cancer, head and neck cancer, breast cancer, ovarian cancer, stomach cancer, lung cancer or a leukemia. The cancer can be metastatic or non-metastatic.

In one aspect, the compound or composition is administered as one or more of: a first line therapy or alternativley, a second line therapy, a third line therapy, or a fourth or subsequent line therapy to administration of a dUPTase-directed therapy. Non-limiting examples of dUTPase-directed therapies include an antimetabolite or a fluoropyrimidine therapy or a 5-FU based adjuvant therapy or an equivalent or each thereof, such as 5-FU, tegafur, gimeracil, oteracil potassium, capcitabine, 5-fluoro-2'-deoxyuridine, methotrexate, or pemetrexed or an equivalent of each thereof.

Certain compounds provided herein demonstrated substantial, such as, 5-100% dUTPase inhibitory effect, an ability to inhibit dUTPase under conditions described herein below, and/or known to the skilled artisan, compared, for example, to a positive control:

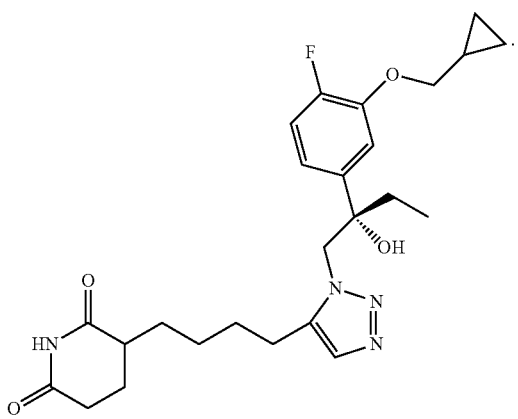

PCI 10851

Kits

The compounds and compositions, as described herein, can be provided in kits. The kits can further contain additional dUTPase inhibitors and optionally, instructions for use. In a further aspect, the kit contains reagents and instructions to perform the screen to identify patients more likely to respond to the therapy as described above.

Screening Assays

This invention also provides screening assays to identify potential therapeutic agents of known and new compounds and combinations. For example, one of skill in the art can also determine if the compound or combination inhibits dUTPase in vitro by contacting the compound or combination with purified or recombinant dUTPase in a cell free system. The purified or recombinant dUTPase and can be from any species, e.g., simian, canine, bovine, ovine, rat, mouse or human. In one aspect, the dUTPase is DUT-N or DUT-M. Isolation, characterization and expression of dUTPase isoforms are disclosed in U.S. Pat. No. 5,962,246 and known in the art.

The contacting can be performed cell-free in vitro or ex vivo with a cell or in a cell culture. When performed in vitro or ex vivo, the compounds, compositions or agents can be directly added to the enzyme solution or added to the cell culture medium. When practiced in vitro or ex vivo, the method can be used to screen for novel combination therapies, formulations or treatment regimens, prior to administration to administration to an animal or a human patient. Methods to quantify inhibition are known in the art, see, U.S. Patent Publ. Nos. 2010/0075924 and 2011/0212467 and U.S. Pat. No. 7,601,702. For example, a fixed dose of a dUTPase directed therapy (e.g., 5-FU or Pemetrexed) can be added to the system and varying amounts of the compound can be subsequently added to system. Alternatively, a fixed dose of a compound of this invention can be added to the system and varying amounts of the dUTPase directed therapy (e.g., 5-FU or Pemetrexed) compound can be subsequently added to system.

In another aspect, the assay requires contacting a first sample comprising suitable cells or tissue ("control sample") with an effective amount of a composition of this invention and optionally a dUTPase inhibitor, and contacting a second sample of the suitable cells or tissue ("test sample") with the agent to be assayed and optionally a dUTPase inhibitor. In one aspect, the cell or tissue over express dUTPase. The inhibition of growth of the first and second cell samples are determined. If the inhibition of growth of the second sample is substantially the same or greater than the first sample, then the agent is a potential drug for therapy. In one aspect, substantially the same or greater inhibition of growth of the cells is a difference of less than about 1%, or alternatively less than about 5% or alternatively less than about 10%, or alternatively greater than about 10%, or alternatively greater than about 20%, or alternatively greater than about 50%, or alternatively greater than about 90%. The contacting can be in vitro or in vivo. Means for determining the inhibition of growth of the cells are well known in the art.

In a further aspect, the test agent is contacted with a third sample of cells or tissue comprising normal counterpart cells or tissue to the control (or alternatively cells that do not over express dUTPase) and test samples and selecting agents that treat the second sample of cells or tissue but does not adversely effect the third sample. For the purpose of the assays described herein, a suitable cell or tissue is described herein such as cancer or other diseases as described herein. Examples of such include, but are not limited to cancer cell or tissue obtained by biopsy, blood, breast cells, colon cells.

Efficacy of the test composition is determined using methods known in the art which include, but are not limited to cell viability assays or apoptosis evaluation.

In yet a further aspect, the assay requires at least two cell types, the first being a suitable control cell.

The assays also are useful to predict whether a subject will be suitably treated by this disclosure by delivering a composition to a sample containing the cell to be treated and assaying for treatment which will vary with the pathology or for screening for new drugs and combinations. In one aspect, the cell or tissue is obtained from the subject or patient by biopsy. Applicants provide kits for determining whether a pathological cell or a patient will be suitably treated by this therapy by providing at least one composition of this invention and instructions for use.

The test cells can be grown in small multi-well plates and is used to detect the biological activity of test compounds. For the purposes of this invention, the successful candidate drug will block the growth or kill the pathogen but leave the control cell type unharmed.

The following examples are included to demonstrate some embodiments of the disclosure. However, those of skill in the art should, in light of the present disclosure, appreciate that many changes can be made in the specific embodiments which are disclosed and still obtain a like or similar result without departing from the spirit and scope of the invention.

EXAMPLE 1

Synthesis of Compounds

Key Intermediate I (S)-1-azido-2-(3-(cyclopropylmethoxy)-4-fluorophenyl)butan-2-ol Key intermediate I was prepared according to the literature data (J. Med. Chem. 2012, 55, 6427).
General Procedure A: Alkylation with LiHMDS

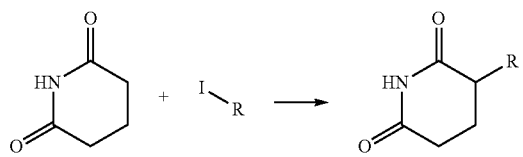

At −40° C., a solution of lithium bis(trimethylsilyl)amide 1 M in tetrahydrofuran (38.9 mmol, 38.9 mL, 2.2 eq) was added dropwise to a solution of glutarimide (2.0 g, 17.7 mmol, 1.0 eq) in tetrahydrofuran (30 mL). The iodoalkane (53.1 mmol, 3.0 eq) was immediately added. After 15 minutes at −40° C., the mixture was allowed to warm up and the mixture was stirred at room temperature for 18 hours. The reaction was quenched with a saturated solution of ammonium chloride (10 mL) and the aqueous phase was extracted with methylene chloride (3×20 mL). The combined organic phases were dried over magnesium sulfate, filtered and evaporated under reduced pressure. The residue was purified by flash chromatography using cyclohexane and ethyl acetate (100/0 to 0/100) to afford the expected compound.
General Procedure B: Alkylation with LDA

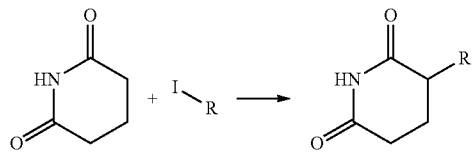

At 0° C., a solution of lithium diisopropylamide 2 M in tetrahydrofuran/heptane/ethylbenzene (38.9 mmol, 19.5 mL, 2.2 eq) was added dropwise to a solution of glutarimide (2.0 g, 17.7 mmol, 1.0 eq) in tetrahydrofuran (30 mL). The iodoalkane (53.1 mmol, 3.0 eq) was immediately added. After 15 minutes at 0° C., the mixture was allowed to warm up and then stirred at room temperature for 18 hours. The reaction was quenched with water (10 mL) and the aqueous phase was extracted with methylene chloride (3×20 mL). The combined organic phases were dried over magnesium sulfate, filtered and evaporated under reduced pressure. The residue was purified by flash chromatography using cyclohexane and ethyl acetate (100/0 to 0/100) to afford the expected compound.
General Procedure C: Reductive Amination

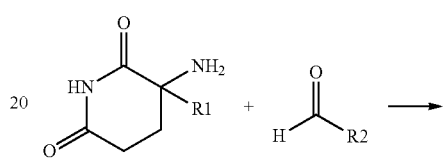

To a solution of the amino compound (HCl Salt) (1.0 eq) in methanol (10 mL) was added a 7 N solution of ammonia in methanol (3.0 eq). The mixture was stirred at room temperature during 15 minutes and acetic acid was added until pH=5. The aldehyde (1.0 eq) and sodium cyanoborohydride (3.0 eq) were added and the mixture was stirred at room temperature for 18 hours. The reaction mixture was carefully quenched with a saturated solution of sodium hydrogenocarbonate (10 mL). The aqueous phase was extracted with ethyl acetate (3×15 mL). The combined organic phases were dried over magnesium sulfate, filtered and evaporated under reduced pressure. The residue was purified by flash chromatography using cyclohexane and ethyl acetate (100/0 to 0/100) to afford the expected compound.
General Procedure D: "Click Chemistry"

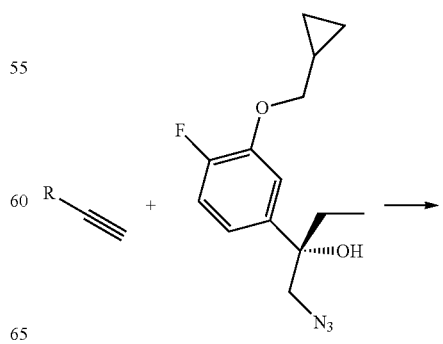

Key intermediate I

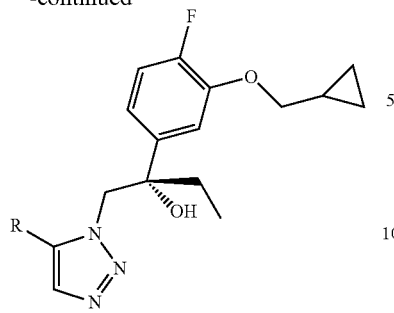

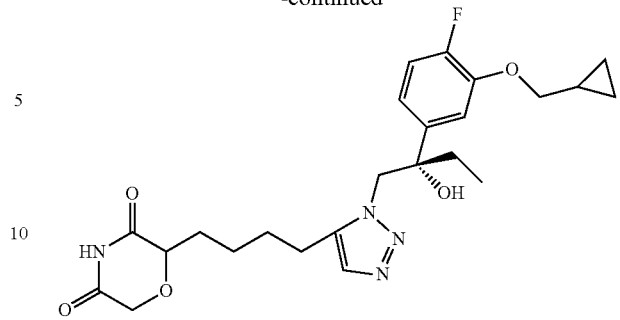

To a solution of the alkynyl compound (1.0 eq) and Key Intermediate I (1.0 eq) in dioxane (10 mL) degazed with argon was added chloro(1,5-cyclooctadiene)(pentamethyl-cyclopentadienyl)ruthenium II (0.1 eq). The reaction mixture was stirred at 80° C. for 3 hours. After cooling down, the reaction mixture was evaporated under vacuum and the residue was absorbed on silica gel to be purified by flash chromatography using cyclohexane and ethyl acetate (100/0 to 0/100) to afford the expected compound.

EXAMPLE 1A 2-(4-{3-[(S)-2-(3-Cyclopropylmethoxy-4-fluoro-phenyl)-2-hydroxy-butyl]-3H-[1,2,3]triazol-4-yl}-butyl)-morpholine-3,5-dione Step 1:
2-hex-5-ynyl-morpholine-3,5-dione was prepared according to General Procedure A using morpholine-3,5-dione (300 mg, 2.6 mmol) and 6-iodo-1-hexyne (1.0 mL, 7.8 mmol). The expected compound was isolated as colorless oil with 12% yield (65 mg).

Step 2:
The title compound was prepared according to General Procedure D, using 2-hex-5-ynyl-morpholine-3,5-dione prepared in step 1 (65 mg, 0.3 mmol) and Key Intermediate I (93 mg, 0.3 mmol). The expected compound was isolated as white solid with 53% yield (83 mg) after purification and lyophilization.

$^1$H NMR (CDCl$_3$): 8.02 (s, 1H), 7.39 (s, 1H), 6.94 (m, 2H), 6.78 (m, 1H), 4.46 (m, 2H), 4.35 (d, J=14.0 Hz, 1H), 4.21 (d, J=14.0 Hz, 1H), 4.06 (m, 1H), 3.79 (d, J=7.0 Hz, 2H), 2.32 (m, 2H), 2.00 (m, 2H), 1.84 (m, 2H), 1.64-1.44 (m, 4H), 1.24 (m, 1H), 0.82 (t, J=7.2 Hz, 3H), 0.62 (m, 2H), 0.34 (m, 2H)

EXAMPLE 1B 4-(4-{3-[(S)-2-(3-Cyclopropylmethoxy-4-fluoro-phenyl)-2-hydroxy-butyl]-3H-[1,2,3]triazol-4-yl}-butyl)-piperazine-2,6-dione

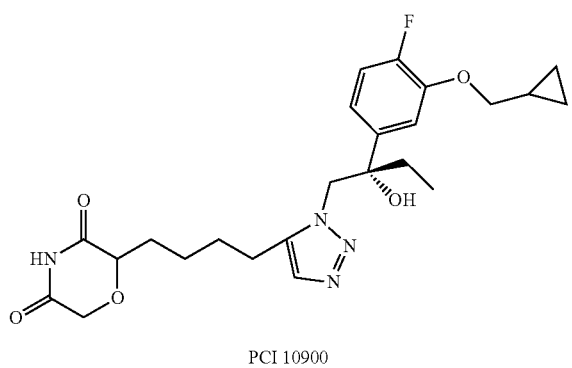

PCI 10900

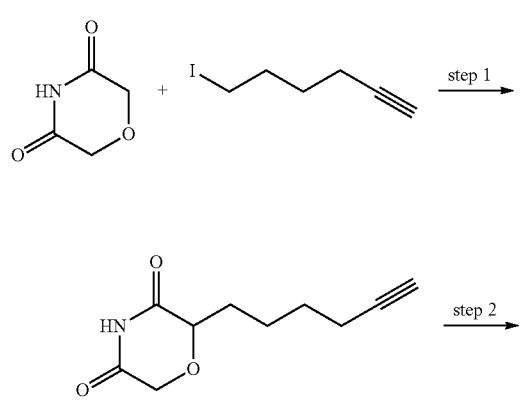

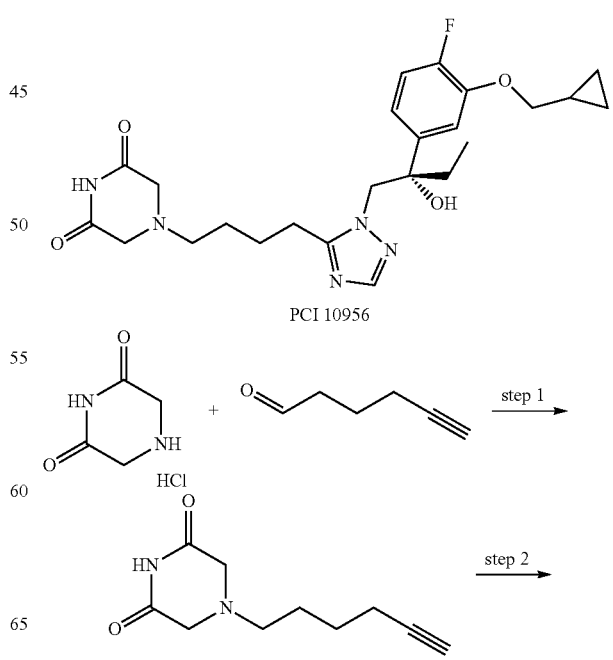

PCI 10956

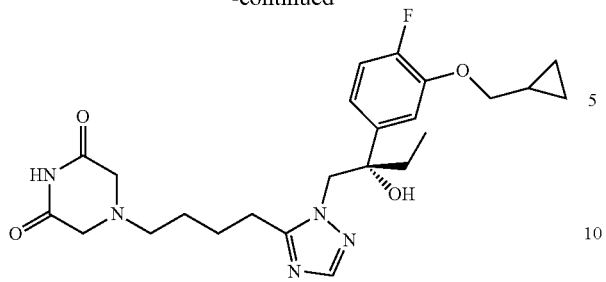

Step 1:
4-hex-5-ynyl-piperazine-2,6-dione was prepared according to General Procedure C using piperazine-2,6-dione hydrochloride (600 mg, 4.0 mmol) and hex-5-ynal (460 mg, 4.8 mmol, 1.2 eq) prepared from hex-5-yn-1-ol according to the procedure described in the literature (US2011/306551). The 4-hex-5-ynyl-piperazine-2,6-dione was isolated with 50% yield (386 mg).

Step 2:
The title compound was prepared according to General Procedure D, using 4-hex-5-ynyl-piperazine-2,6-dione prepared in step 1 (150 mg, 0.8 mmol) and Key Intermediate I (216 mg, 0.8 mmol). The expected compound was obtained as white powder after purification and lyophilization with 27% yield (100 mg).

$^1$H NMR (DMSO): 11.10 (s, 1H), 7.38 (s, 1H), 7.07 (dd, J=8.5 and 11.3 Hz, 1H), 6.93 (dd, J=2.0 and 8.5 Hz, 1H), 6.83 (m, 1H), 5.29 (s, 1H), 4.41 (s, 2H), 3.78 (d, J=7.0 Hz, 2H), 3.27 (s, 4H), 2.29 (m, 4H), 1.99 (m, 1H), 1.77 (m, 1H), 1.58-1.38 (m, 4H), 1.17 (m, 1H), 0.69 (t, J=7.2 Hz, 3H), 0.55 (m, 2H), 0.31 (m, 2H)

EXAMPLE 1C 4-(3-{3-[(S)-2-(3-Cyclopropylmethoxy-4-fluorophenyl)-2-hydroxy-butyl]-3H-[1,2,3]triazol-4-yl}-propionyl)-piperazine-2,6-dione

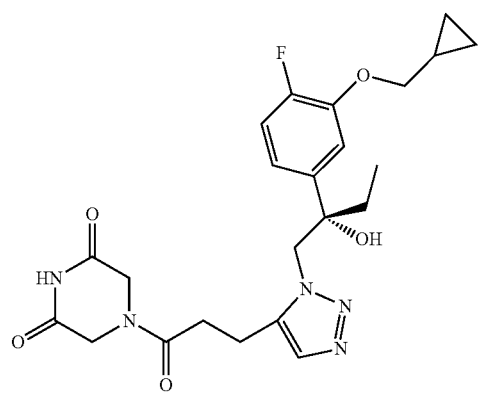

PCI 10976

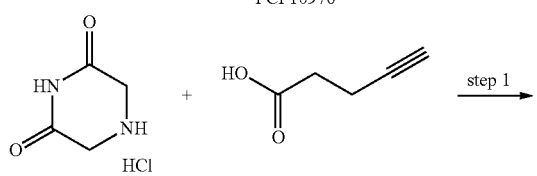

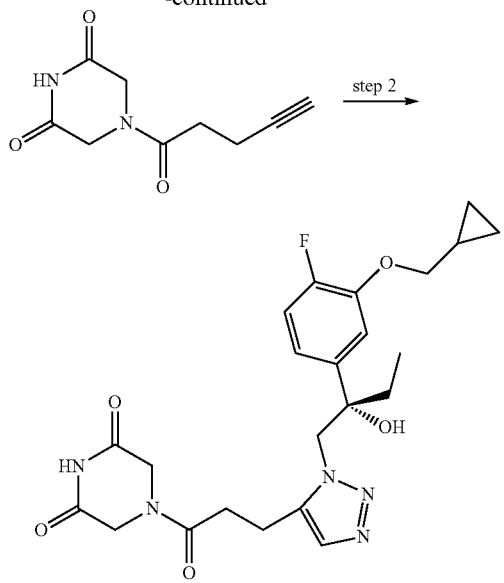

Step 1:
To a solution of piperazine-2,6-dione hydrochloride (1.0 g, 6.6 mmol) in methylene chloride (50 mL) was added pent-4-ynoic acid (782 mg, 8.0 mmol, 1.2 eq), HOBt (1.2 g, 8.0 mmol, 1.2 eq), EDCI (1.5 g, 8.0 mmol, 1.2 eq) and DIEA (3.4 mL, 19.9 mmol, 3.0 eq). The reaction mixture was stirred at room temperature for 18 hours. Water (15 mL) was added and the aqueous phase was extracted with methylene chloride (1×10 mL) and ethyl acetate (2×10 mL). The combined organic phases are dried over magnesium sulfate, filtered and evaporated under reduced pressure. The residue was purified by flash chromatography using cyclohexane and ethyl acetate (100/0 to 0/100) to afford 4-pent-4-ynoyl-piperazine-2,6-dione as white solid with 56% yield (725 mg).

Step 2:
The title compound was prepared according to General Procedure D, using 4-pent-4-ynoyl-piperazine-2,6-dione prepared in step 1 (150 mg, 0.8 mmol) and Key Intermediate I (216 mg, 0.8 mmol). The lyophilization of the purified residue afforded the expected compound as off-white solid with 46% yield (169 mg).

$^1$H NMR (DMSO): 11.36 (s, 1H), 7.44 (s, 1H), 7.08 (dd, J=8.5 and 11.3 Hz, 1H), 6.93 (dd, J=1.9 and 8.4 Hz, 1H), 6.86 (m, 1H), 5.30 (s, 1H), 4.51 (d, J=14.2 Hz, 1H), 4.44 (d, J=14.2 Hz, 1H), 4.31 (m, 2H), 4.24 (m, 2H), 3.81 (d, J=7.0 Hz, 2H), 2.65 (m, 4H), 1.99 (m, 1H), 1.74 (m, 1H), 1.17 (m, 1H), 0.66 (t, J=7.2 Hz, 3H), 0.55 (m, 2H), 0.35 (m, 2H)

Other compounds of formula (I) and (II) are prepared in an analogous manner. In some cases, protection of the "NH" group on the piperidine-2,4-dione is required.

EXAMPLE 2

Preparation of Stereochemically Pure Compounds

The disclosed compounds can exist as two diastereomers. This example demonstrates a separation protocol. The stereochemical pure compounds are prepared and then tested to determine if the biological activity is attributed to one or both stereoisomers.

Separation of the diastereomers is performed by preparative chiral high performance liquid chromatography (HPLC) employing a 250×30 mm CHIRALPAK IA (5 μm) column, heptane/iso-propanol (70/30) with a flow-rate of 42.5 mL/min and UV detection (λ=270 nm at 25° C.). Analytical chiral HPLC is performed employing a 250×4.6 mm CHIRALPAK IA (5 μm) column, heptane/iso-propanol/diethylamine (70/30/0.1) with a flow rate of 1 mL/min and UV detection (λ=230 nm at 25° C.).

EXAMPLE 3

Biological Methods

A. Drugs, Reagents and Cell Lines

Test compounds are suspended in DMSO at a concentration, e.g., of 100 mmol/L, fluorodeoxyuridine (FUdR) that can be obtained from Sigma (St Louis, Mo.) and maintained in sterile double-distilled water at stock concentrations of 50 mmol/L.

Recombinant human deoxyuridine nucleotidohydrolase (dUTPase) is expressed and purified as described in Ladner R D, Carr S A, Huddleston M J, McNulty D E, Caradonna S J. J Biol Chem. 1996 Mar. 29; 271(13):7752-7. All drugs stocks are aliquoted and diluted as appropriate prior to use. The oligonucelotide primer, templates and fluorophore- and quencher-labeled detection probes are synthesized by Integrated DNA Technologies (Coralville, Iowa), subjected to polyacrylamide gel electrophoresis purification and reconstituted in Omnipur sterile nuclease-free water (EMD Chemicals USA, Gibbstown N.J.) at a stock concentration of 100 μmol/L. The two non-emissive (dark) quenching molecules incorporated into the detection probes include the Iowa black fluorescein quencher (IBFQ; absorption max 531 nm) and ZEN (non-abbreviation; absorption max 532 nm). The fluorescent label utilized is 6-FAM (5"-carboxyfluorescein; excitation max.=494 nm, emission max.=520 nm). Probes are further diluted to a working stock of 10 μmol/L and aliquoted to avoid repeated freeze/thaw cycles. AmpliTaq Gold DNA Polymerase, GeneAmp 10×PCR Buffer 2, $MgCl_2$ and MicroAmp Optical 96-well Reaction Plates are purchased from Applied Biosystems (Carlsbad, Calif.). dNTPs are purchased individually at stock concentrations of 100 mmol/L from New England Biolabs at HPLC-certified >99% purity (Ipswich, Mass.).

B. Assay Components, Instrumentation and Real-time Fluorescence Conditions

Reaction mixtures contained primer, probe and template at an equimolar final concentration of 0.4 μmol/L. Magnesium chloride ($MgCl_2$) is included at a final concentration of 2 mmol/L. Non-limiting dNTPs are included in the reaction mix in excess at a final concentration of 100 μmol/L (dUTP/dTTP is excluded). AmpliTaq Gold DNA polymerase is added at 0.875 U/reaction, 2.5 μl of 10×PCR buffer 2 added and nuclease-free dd$H_2O$ added to a final reaction volume of 25 μl. For dUTP inhibition analysis, the volume of dd$H_2O$ is further modified to accommodate an additional 1 μl of dUTPase (10 ng/μl) and 1 μl of inhibitor or DMSO control. Thermal profiling and fluorescence detection is performed using the 'isothermal' program on board an Applied Biosystems 7500 Real-Time PCR System. For analysis of dNTPs, the thermal profile consisted of an 8 min 37° C. step followed by a 10 min 95° C. step to 'hot-start' the Taq polymerase and a primer extension time of up to 30 min at 60° C. depending on the application. Raw fluorescence spectra for 6-FAM is measured using filter A at specified time intervals to follow assay progression using Sequence Detection Software (SDS Version 1.4, Applied Biosystems) and exported and analyzed in Microsoft Excel (Microsoft, Redmond Wash.) and Prism (GraphPad Software, La Jolla Calif.). Fluorescence values for blank reactions (limiting dNTP omitted) are subtracted to give normalized fluorescence units (NFU) to account for background fluorescence.

C. MTS Growth Inhibition Assay

The Cell Titer AQueous MTS assay (Promega) is carried out according to the manufacturers guidelines. $IC_{50(72h)}$ values are calculated from sigmoidal-dose response curves utilizing Prism (Graphpad, San Diego, Calif.). The combination effect is determined by the combination index (CI) method utilizing Calcusyn software (Biosoft, Ferguson, Mo.). Fraction affected (FA) is calculated from the percent growth inhibition: FA=(100–% growth inhibition)/100. CI values <1, synergism; 1-1.2, additive and >1.2, antagonism.

D. Colony Formation Assay

Colony forming assay showing the ability of colon (SW620, HCT116), non-small cell lung (A549, H460, H1299 and H358) and breast (MCF7) cancer cells to survive and proliferate following transient 24 hour exposure to test compounds, FUdR and combinations are determined. Specifically, cells are seeded at densities between 50 and 100 cells/well in 24-well plates. Twenty-four hours later, cells are treated with increasing concentrations of a rtest compound, a fixed dose of FUdR and combinations of these. After 24 hours, drug is removed, cells are rinsed and allowed to outgrow for 10-14 days. At the conclusion of the outgrowth, cells are fixed in 60% ice cold methanol and stained with 0.1% crystal violet, scanned and counted. Data is presented as percentage of untreated controls (mean±SD). Fraction affected and combination indexes are calculated according to the method of Chou and Talalay where <1 is indicative of a synergistic drug interaction.

E. In Vivo Analysis

Xenograft experiments are conducted in male NU/NU nude mice (Charles River, Wilmington, Mass.) that are 6-8 weeks old. Subcutaneous A549 xenografts are established and allowed to grow until they reached ~50 $mm^3$ (day 1). Animals are randomized to treatment groups: vehicle, pemetrexed 50 mg/kg, a test compound and combination of pemetrexed plus a test compound (n=5, group). Pemetrexed is administered at 50 mg/kg by intraperitoneal injection every two days. Test compound is administered, e.g., at 75 mg/kg by intraperitoneal injection every two days. The combination of pemetrexed and the test compound is administered by intraperitoneal injection, e.g., every two days. Two perpendicular diameters of tumors are measured every 2 days with a digital caliper by the same investigator. Tumor volume is calculated according to the following formula: TV ($mm^3$)=(length[mm]×(width $[mm]^2$)/2. Mice are inspected everyday for overall health and bodyweight is measured every 2 days as an index of toxicity. All animal protocols are approved by the USC Animal Care and Use Committee (IACUC).

EXAMPLE 4 dUTPase Inhibition

Test compounds are screened in a fluorescence-based assay. The assay employs a DNA polymerase-based approach utilizing an oligonucleotide template with 3 distinct regions: a 3' primer binding region, a mid-template dUTP/thymidine triphosphate (TTP) detection region and a 5' 6-Flavin adenine mononucleotide (FAM)-labeled probe binding region that incorporates a black hole quenching moiety. During the reaction, the probe and primer hybridize to the oligonucleotide template to form the template:primer:probe complex. When Taq polymerase binds to the primer in the TPP complex and dUTP is present, successful extension of the nascent strand occurs and the inherent 5' to 3' exonuclease activity of Taq polymerase cleaves and displaces the 6-FAM-labeled probe in a 5' to 3' direction, releasing the 6-FAM fluorophore from its proximity to the three quenchers. This displacement effectively disrupts the Förster resonance energy transfer (FRET) and the resulting fluorescence detected upon excitation is directly proportional to the amount of the dUTP available in the assay for incorporation. Conversely, when the dUTP is unavailable, exhausted, or degraded by dUTPase and is no longer available for incorporation, Taq polymerase stalls and extension delay and/or chain termination of the nascent strand occurs. In this instance, probe hydrolysis/degradation does not occur and the probe remains dark as fluorescence remains quenched via FRET. Since fluorescence is directly proportional to the concentration of dUTP, the assay is easily modified to measure dUTP and the effects of inhibitors on dUTP hydrolysis by the enzyme dUTPase. The template BHQ-DT6 (Black Hole Quencher—Detection Template 6) for detecting up to 60 pmols of dUTP is included for this application of the assay along with 50 pmols of dUTP and 5 ng of recombinant dUTPase. The reaction is incubated at 37° C. for 8 mins and terminated by a 10 min incubation at 95° C. to simultaneously inactivate dUTPase and activate the hot-start Taq polymerase. The fluorescence generated during the detection step is directly proportional to the concentration of dUTP remaining after the 8 min incubation. The concentration of dUTP at reaction termination and therefore inhibition of dUTPase in the presence and absence of inhibitors and appropriate dimethyl sulfoxide (DMSO) controls can be determined.

EXAMPLE 5

Test compounds are evaluated for their antitumor activity in colorectal cancer cells using the MTS growth inhibition assay. HCT116 and SW620 cells are exposed to increasing concentrations of each agent for 72 hours and growth inhibition is directly compared to vehicle-treated controls. The NSCLC cell lines A549 and H1299 are exposed to increasing concentrations of each agent for 72 hours and growth inhibition is directly compared to vehicle-treated controls.

EXAMPLE 6

Growth Inhibition

MTS growth inhibition assays are performed to evaluate the effectiveness of the test compounds alone and in combination with the fluoropyrimidine thymidylate synthase (TS) inhibitor 5-fluorouracil (5-FU) at inhibiting the growth of colorectal (HCT116 and SW620) cell line models. Increasing concentrations of 5-FU between 0 and 100 μmol/L demonstrated dose-dependent increases in growth inhibition in both the colorectal cancer cell lines evaluated. Simultaneous treatment with increasing concentrations of 5-FU and a test compound at fixed concentrations of 25 μmol/L is determined.

EXAMPLE 7

Reducing Cancer Cell Viability

Colony forming assays are performed to evaluate the effectiveness of test compounds alone and in combination with the fluoropyrimidine thymidylate synthase (TS) inhibitor fluorodcoxyuridinc (FUdR) at reducing cancer cell viability in colorectal (HCT116), breast (MCF-7) and non-small cell lung (H1299, A549, H358 and H460) cell line models. Increasing concentrations of FUdR between 0.5 and 2.5 μmon demonstrated dose-dependent decreases in colonies formed in all cell lines evaluated. In colorectal cancer cells, concentrations of test compounds ranging e.g., from 3.1 μmol/L to 50 μmol/L are combined with 0.5 μmol/L FUdR in HCT116 cells and 1 μmol/L FUdR in SW620 cells.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The invention has been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

The invention claimed is:
1. A compound of formula (I):

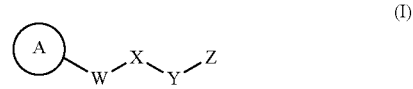

or a tautomer thereof, including any stereoisomer, enantiomer or diastereoisomer, or a pharmaceutically acceptable salt and/or a solvate of each thereof, of formula (I):

or a tautomer thereof, or a pharmaceutically acceptable salt of each thereof, wherein

is

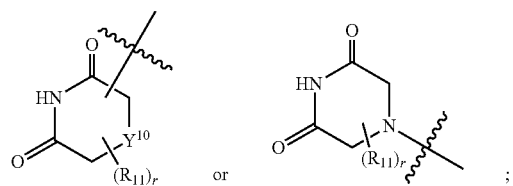

$Y^{10}$ is O, S, SO, SO$_2$, NH or NR$^{15}$;

R$_{11}$ is hydrogen, halo, R$^{12}$ or —O—R$^{12}$, wherein R$^{12}$ is C$_1$-C$_6$alkyl, C$_2$-C$_6$ alkenyl, or C$_2$-C$_6$ alkynyl optionally substituted with 1-3 hydroxy, fluoro, chloro, and amino substituent, or R$_{11}$ is C$_1$-C$_6$ alkyl, C$_2$-C$_6$ alkenyl, or C$_2$-C$_6$ alkynyl wherein each alkyl, alkenyl, and alkynyl is optionally substituted with 1-3 hydroxy, fluoro, chloro, and amino substituent;

r is 1, 2, or 3;

$R^{15}$ is $C_1$-$C_6$ alkyl optionally substituted with 1-3 $C_1$-$C_6$ alkoxy, hydroxy, amino, and oxo groups;

W is a bond or optionally substituted —$CH_2$—;

X is a bond, O, S, $NR^{19}$, optionally substituted $C_1$-$C_6$ alkylene, optionally substituted $C_2$-$C_6$ alkenylene, or optionally substituted $C_1$-$C_6$ alkynylene group, a divalent optionally substituted $C_6$-$C_{10}$ aromatic hydrocarbon group, or a divalent optionally substituted saturated or unsaturated $C_2$-$C_{10}$ heterocyclic or optionally substituted $C_1$-$C_{10}$ heteroaryl group;

$R^{19}$ is hydrogen, optionally substituted $C_1$-$C_6$ alkyl or optionally substituted $C_3$-$C_8$ cycloalkyl;

Y is an optionally substituted $C_1$-$C_{10}$ alkylene which further optionally has a cycloalkylidene structure on one carbon atom, or is optionally substituted $C_2$-$C_6$ alkenylene, or optionally substituted $C_2$-$C_6$ alkynylene group, or Y is -$L^{10}$-$B^1$-$L^{11}$-;

$L^{10}$ and $L^{11}$ independently are optionally substituted $C_1$-$C_6$ alkylene, optionally substituted $C_2$-$C_6$ alkenylene, or optionally substituted $C_2$-$C_6$ alkynylene group;

$B^1$ is a divalent optionally substituted $C_1$-$C_{10}$ heteroaryl group;

Z is —$SO_2NR^{31}R^{32}$, —$NR^3SO_2$—$R^4$, or $R^4$ wherein $R^{31}$ and $R^{32}$ are the same or different and each represents a hydrogen atom, optionally substituted $C_1$-$C_6$ alkyl group optionally substituted with an aryl group;

$R^3$ is hydrogen or optionally substituted $C_1$-$C_6$ alkyl; and $R^4$ is optionally substituted $C_6$-$C_{10}$ aryl, an optionally substituted $C_2$-$C_{10}$ heterocyclic group, or an optionally substituted $C_1$-$C_{10}$ heteroaryl group;

provided that if W is a bond, X cannot be a bond.

2. The compound of claim 1, wherein each $R^{19}$ independently is hydrogen or methyl.

3. The compound of claim 1, wherein the uracil isostere A is:

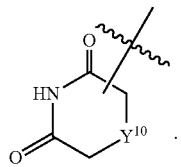

4. The compound of claim 1, wherein the uracil isostere A is:

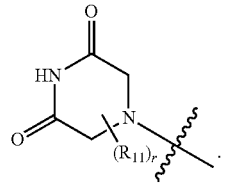

5. The compound of claim 1 of formula:

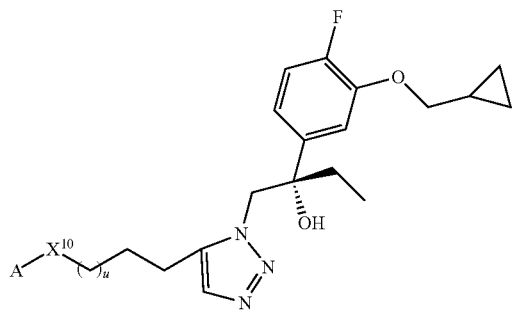

wherein A is:

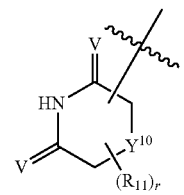

$R_{11}$ is hydrogen, halo, $R^{12}$ or —O—$R^{12}$, wherein $R^{12}$ is $C_1$-$C_6$ alkyl, $C_2$-$C_6$ alkenyl, or $C_2$-$C_6$ alkynyl optionally substituted with 1-3 hydroxy, fluoro, chloro, and amino substituent, or $R^{11}$ is $C_1$-$C_6$ alkyl, $C_2$-$C_6$ alkenyl, or $C_2$-$C_6$ alkynyl wherein each alkyl, alkenyl, and alkynyl is optionally substituted with 1-3 hydroxy, fluoro, chloro, and amino substituent;

r is 1, 2, or 3, $Y^{10}$ is O, S, SO, $SO_2$, NH or $NR^{15}$, or $X^{10}$ is joined at $Y^{10}$ with $Y^{10}$ being a nitrogen atom;

$R^{15}$ is $C_1$-$C_6$ alkyl optionally substituted with 1-3 $C_1$-$C_6$ alkoxy, hydroxy, amino, and oxo groups;

$X^{10}$ is NH, O, or $CH_2$; and u is 0, 1, 2, 3, or 4.

6. The compound of claim 5, wherein A is:

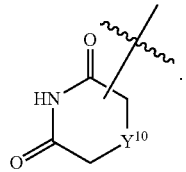

7. The compound of claim 5, wherein A is:

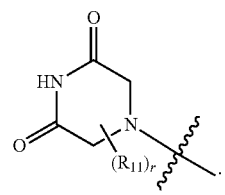

* * * * *